United States Patent [19]

Fisher et al.

[11] Patent Number: 4,855,290

[45] Date of Patent: Aug. 8, 1989

[54] DERIVATIVES OF QUINUCLIDINE

[75] Inventors: Abraham Fisher, Holon; Ishai Karton, Ness-Ziona; Eliahu Heldman, Rehovot; Aharon Levy, Moshav Beith Hanan; Yona Grunfeld, Rehovot, all of Israel

[73] Assignee: State of Israel, represented by Prime Minister's Office, Israel Institute for Biological Research, Ness-Ziona, Israel

[21] Appl. No.: 853,404

[22] Filed: Apr. 18, 1986

[30] Foreign Application Priority Data

May 10, 1985 [IL] Israel ............................... 75166
Jan. 10, 1986 [IL] Israel ............................... 77568

[51] Int. Cl.$^4$ ................. C07D 497/20; A61K 31/435
[52] U.S. Cl. ........................... 514/278; 546/18; 546/19
[58] Field of Search ................ 546/18, 19; 514/278

[56] References Cited

U.S. PATENT DOCUMENTS 4,104,397  8/1978  Cohen et al. ................ 546/18

FOREIGN PATENT DOCUMENTS 2146962  9/1973  France ........................... 546/18
1301254 12/1972  United Kingdom ........... 546/18

OTHER PUBLICATIONS

Noller, "Chemistry of Organic Compounds", 2nd edition (1957) (Saunders) pp. 203–204, 278, 744–745.
Royals, "Advanced Organic Chemistry" (1954) (Prentice-Hall) pp. 627–639.
Mar., "Advanced Organic Chemistry" (1968) (McGraw-Hill) pp. 319, 328, 661, 662, 655.
Takemura et al., "Synthesis and Selective Activity of Cholinergic Agents with Rigid Skeletons II", 29 *Chem. Pharm. Bull.*, No. 10, pp. 3019–3025.

*Primary Examiner*—Robert T. Bond
*Attorney, Agent, or Firm*—Cushman, Darby & Cushman

[57] ABSTRACT

Quinuclidine derivatives having the general formula (I)

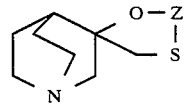

and geometrical isomers, enantiomers, diastereoisomers, racemates and/or acid addition salts thereof, wherein Z represents the group $>CR^1R^2$ or two hydrogen atoms; and $R^1$ and $R^2$, which may be identical or different, are each alkyl, cyclopentyl, cyclohexyl, aryl, or diarylmethylol, or alkyl which is substituted by one or more aryl groups, or one of $R^1$ and $R^2$ may be hydrogen.

67 Claims, 19 Drawing Sheets

FIG. 1
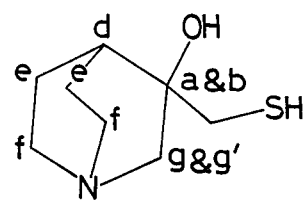
SOLVENT; CDCl$_3$
250 MHz NMR
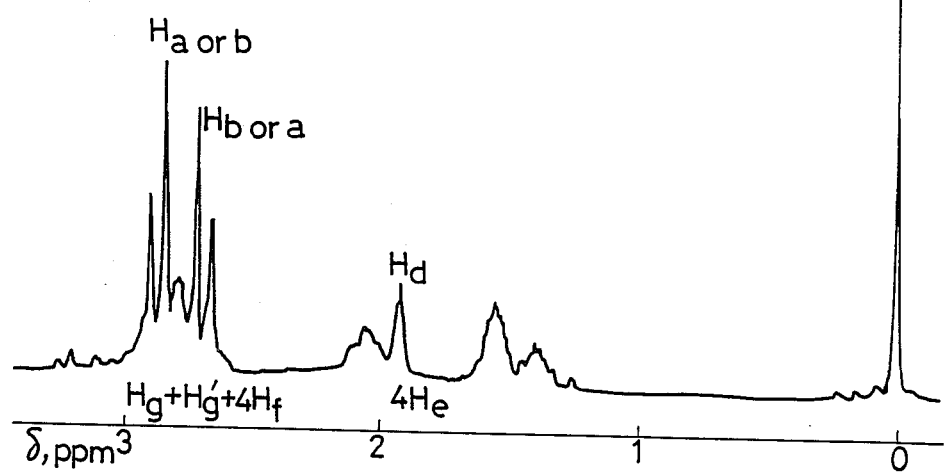

FIG. 2
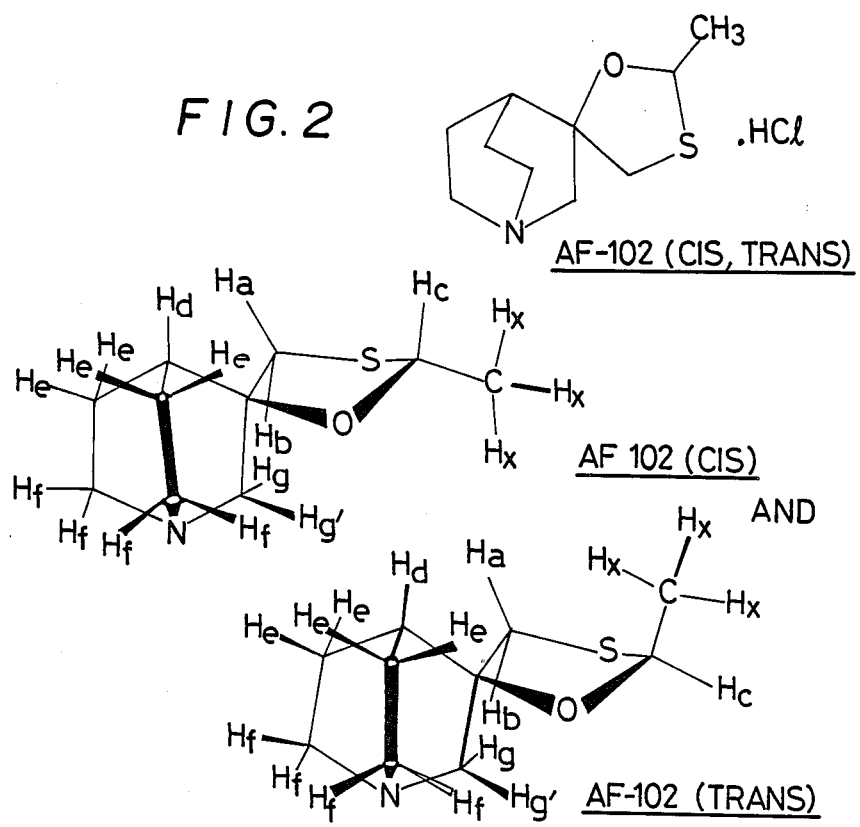
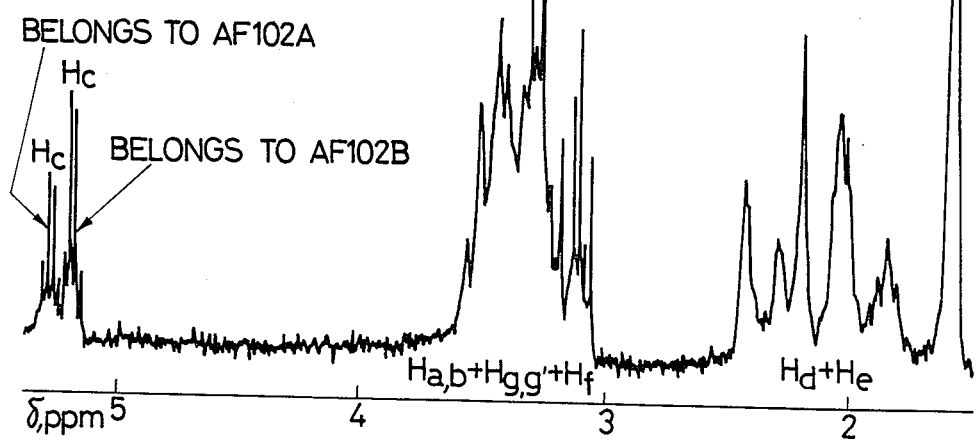

DERIVATIVES OF QUINUCLIDINE

FIELD OF THE INVENTION

The present invention relates to novel spiro(1,3-oxathiolane-5,3')quinuclidines and a novel hydroxymercaptomethylquinuclidine; processes for preparing the novel compounds; pharmaceutical compositions containing the spiro-compounds; and a method for treating diseases of the central nervous system using such spiro-compounds or pharmaceutical compositions.

BACKGROUND OF THE INVENTION

U.S. Pat. No. 4,083,985 describes a range of fused-ring quinuclidines which are described as psychomotor stimulators, and which may be regarded structurally as a quinuclidine nucleus fused to a cyclohexanone, cyclohexenone or delta-lactone moiety. These compounds are stated to be useful for treating (inter alia) Parkinsons' Disease and depression, and evidently possess anticholinergic activity. There is no indication in this Patent that any of these compounds possess cholinergic activity.

U.S. Pat. No. 4,104,397 describes spiro(1,3-dioxolane-4,3')quinuclidines which may have one or two alkyl and/or aryl substituents in the 2-position of the dioxolane ring. The Patent specifically describes the monomethyl, dimethyl and diphenyl compounds. The monomethyl compound is shown to have cholinergic activity and the diphenyl compound to have anticholinergic activity. The nature of the pharmacological activity exhibited by the other compounds embraced by this Patent is not described therein.

A chronic deficiency in vivo in central cholinergic function, that is to say in the function of acetylcholine as a neurotransmitter, has been implicated in a variety of neurologic and psychiatric disorders, including senile dementia of Alzheimer's type(SDAT), tardive dyskinesia, Pick's disease, Huntington's chorea, Gilles de la Tourette disease, Friedrich's ataxia, and Down's syndrome. Clinical data indicate that cholinergic transmission may have been compromised in persons affected with these diseases (Fisher and Hanin, Life Sciences, 27: 1615, 1980).

Among these disorders, SDAT is the most widespread neuropsychiatric disease (for reviews see Schneck et al, Am. J. Psychiatry, 139: 165, 1982 and Coyle et al, Science 219: 1184, 1983). The development of an effective treatment for SDAT is one of the most pressing needs facing medicine today. This age-related disease is becoming increasingly prevalent as the population of the elderly grows in line with the progressively higher life expectancy of the older population.

SDAT is characterized morphologically by an increased number of senile plaques in selected brain areas; biochemically by a significant reduction in presynaptic cholinergic markers in the same brain areas, the cortex and the hippocampus in particular; and behaviorally by a loss of cognitive functions in individual patients.

Since SDAT appears to be associated with brain cholinergic hypofunction, trials have been conducted in which ACh precursors (choline or lecithin), acetylcholinesterase inhibitors (physostigmine or tetrahydroaminoacridine) or direct acting muscarinic agonists (arecoline) have been administered to SDAT patients because of the ability of these agents to elevate, and thus presumably restore cholinergic activity in the brain. To date, the results have not been conclusive as to the efficacy of treatment with the above-mentioned agents; this is due mainly to unwanted side-effects, narrow therapeutic window, or lack of therapeutic efficacy.

There is an urgent need for drugs which are effective in the treatment of SDAT. Progress in this area has been hindered by the lack of adequate animal models that can mimic directly the cholinergic abnormality implicated in SDAT, and by a dearth of long-acting central cholinergic agonists which can discriminate among subclasses of receptors, and primarily activate those that are involved in cognitive functions. Most known cholinergic agonists (muscarinic drugs) have undesirable side-effects. A long-lasting, centrally active cholinomimetic drug without peripheral side effects would therefore be most useful. The R & D of such drugs would require their evaluation in suitable animals models for SDAT.

In this context, we have recently developed a selective presynaptic cholinergic neurotoxin, ethylcholine aziridinium ion (AF64A), which on intracerebroventricular injection in rats induces persistent cholinergic hypofunction that mimics the cortical and hippocampal cholinergic deficiency and the cognitive impairments reported in SDAT. This animal model could be extremely useful in developing novel treatment approaches for SDAT. (Fisher et al in Behavorial Models and the Analysis of Drug Action, eds. Spiegelstein and Levy, Elsevier, Amsterdam, 1983, p. 333; Fisher and Hanin, Ann. Rev. Pharmacol. Toxicol., 26: 161–81 (1986).

The availability of centrally active muscarinic compounds which have long acting central cholinergic activity without significant peripheral adverse side-effects capable of reversing cognitive impairments induced by AF64A in rats, could be extremely useful in treating SDAT and the above-mentioned related disease states.

Therapeutically active oxathiolane compounds and their pharmacology are relatively little known. Moreover, the literature is replete with unsuccessful attempts to replace a particular atom or group in a pharmacologically active chemical compound by a supposedly analogous atom or group, in an attempt to improve the therapeutic profile of the original compound. Thus, in replacing for example an oxygen-atom by a sulfur atom which has twice the atomic mass of oxygen, the result in pharmacological terms cannot be predicted with any degree of certainty.

However, we have now surprisingly discovered, and this discovery forms the basis of the present invention, that if in the spiro(dioxolane)quinuclidines of U.S. Pat. No. 4,104,397, the oxygen atom of the dioxolane ring which is more remote from the quinuclidine nucleus is replaced by a sulfur atom, and at the same time the ambit of the substituents at the 2-position is extended to include diarylmethylol, and alkyl substituted by aryl, then (i) the most active isomer of the monomethyl compound, while possessing a not dissimilar activity (measured by the Guinea-pig ileum induced contraction and muscarinic receptor binding tests) as compared with that of the most active isomer of the analogue disclosed in the aforementioned U.S. Patent, however exhibits significantly less pronounced side-effects (sialogenic and tremorigenic activity) than the latter compound under similar conditions; and (ii) the most active isomer of the monomethyl compound has interesting potential for the treatment of SDAT as shown by the tests on animal models mentioned above.

On the other hand, the vast majority of the other 2-substituted members of the series containing the sulfur atom in place of oxygen as aforesaid, and in particular those members containing at least one 2-substituent which is alkyl having three or more carbon atoms, cyclopentyl, cyclohexyl, aryl, diarylmethylol or alkyl substituted by aryl, have anticholinergic activity, as contrasted with the cholinergic activity of the monomethyl compound.

SUMMARY OF THE INVENTION

The invention accordingly provides quinuclidine derivatives having the general formula (I)

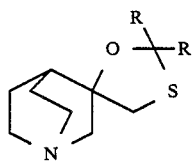

and geometrical isomers, enantiomers, diastereoisomers, racemates and/or acid addition salts thereof, wherein $R^2$, which may be identical or different, are each alkyl, cyclopentyl, cyclohexyl, aryl, or diarylmethylol, or alkyl which is substituted by one or more aryl groups, or one of $R^1$ and $R^2$ may be hydrogen.

In accordance with one embodiment of the invention, one of $R^1$ and $R^2$ is hydrogen, and the other of $R^1$ and $R^2$ is alkyl, cyclopentyl, cyclohexyl, aryl, or diarylmethylol, or alkyl which is substituted by one or more aryl groups.

In accordance with a further embodiment of the invention, one of $R^1$ and $R^2$ is alkyl, cyclopentyl or cyclohexyl, and the other of $R^1$ and $R^2$ is alkyl, cyclopentyl, cyclohexyl, aryl, or diarylmethylol, or alkyl which is substituted by one or more aryl groups.

In accordance with still a further embodiment of the invention, one of $R^1$ and $R^2$ is aryl, and the other of $R^1$ and $R^2$ is aryl or diarylmethylol, or alkyl which is substituted by one or more aryl groups.

The compounds of the formula (I) thus defined have central nervous system activity. These compounds may be named as 2,2-disubstituted spiro(1,3-oxathiolane-5,3')quinuclidines. Non-limiting examples of such compounds are described in the following table:

| one of $R^1$ and $R^2$ | the other of $R^1$ and $R^2$ |
|---|---|
| hydrogen | methyl (Ia) |
| hydrogen | ethyl |
| hydrogen | propyl |
| hydrogen | phenyl |
| hydrogen | 1-pyrenepropyl |
| hydrogen | diphenylmethyl (Ib) |
| hydrogen | diphenylmethylol |
| methyl | phenyl (Ic) |
| ethyl | phenyl |
| cyclohexyl | phenyl |
| phenyl | phenyl |

The invention also includes the compound 3-hydroxy-3-mercaptomethylquinuclidine, from which the compounds of formula (I) may be prepared.

As previously indicated, the invention includes the geometrical isomers, enantiomers, diastereoisomers, racemates and/or acid addition salts, of the compounds of formula (I).

It will be appreciated that geometrical isomerism arises from the fact that in the spiro-compounds of the invention, $R^1$ for example, may be either on the same side of the oxathiolane ring as the nitrogen atom of the quinuclidine ring, or on the opposite side. If, in the spiro-compounds of the invention, $R^1$ and $R^2$ are identical, then there will be a single centre of asymmetry at the 5,3'(spiro) carbon atom, this will also give rise to enantiomers and the racemaftes thereof. If, on the other hand, $R^1$ and $R^2$ in the spiro-compounds are not identical, then there will be a further centre of asymmetry at the 2-position of the oxathiolane ring, thus giving rise to diastereoisomers and the racemates thereof, in addition to the geometrical isomers already mentioned. It will moreover be appreciated, that in the compound of the present invention which is 3-hydroxy-3-mercaptomethylquinuclidine, there exists no possibility of geometrical isomerism; here also, however, there is a centre of asymmetry at the 3-position of the quinuclidine ring, thus giving rise to enantiomeric and racemic forms.

The compounds of formula (I), whether as isomeric mixtures or compounds, or whether as individually isolated geometric or optical isomers, form stable addition salts with organic or inorganic acids, as for example with hydrochloric acid. It will be observed that, while for therapeutic application such salts should be pharmaceutically compatible, nevertheless it may be convenient, as for example for purposes of isolation, to employ acid addition salts which are not pharmaceutically compatible, and the invention relates also to the acid addition salts of the latter kind. As will be obvious to those skilled in the art, if the compounds are obtained e.g. as a result of isolation from their process of preparation in the form of free bases, they may be converted to the acid addition salts by reaction with the appropriate acid, and conversely, the compounds isolated in the form of their acid addition salts may be converted by reaction with a base, such as alkali metal hydroxide, to the corresponding free bases.

Geometrical isomers are generally isolated by a physical method such as fractional crystallization (of the isomers per se, or of their salts), fractional distillation or column chromatography (using high or low pressure liquid chromatography techniques), while optical isomers are isolated by forming a salt mixture with an optically active complementary reagent (in the present case an optically active acid), followed by fractionation of the mixture, and isolation of the desired optical isomers from the salt fractions.

In a particular embodiment, the invention provides the isolated geometrical isomers of the compound wherein one of $R^1$ and $R^2$ is hydrogen and the other of $R^1$ and $R^2$ is methyl(Ia). These isomers may be differentiated from each other by the fact that their salts with hydrochloric acid have quite distinct relatively higher and relatively lower melting-points. The hydrochloric acid salt of the mixture of geometrical isomers of compound (Ia) which is isolated from the preparative process of the invention, as well as the hydrochloric acid salts of the individual geometrical isomers are also included within the scope of the invention.

In accordance with the invention, the compounds of formula (I) are prepared by a process which comprises reacting 3-hydroxy-3-mercaptomethylquinuclidine with a carbonyl compound of formula $R^1$—CO—$R^2$, and isolating the desired product from the reaction mixture. The process is desirably carried out in the presence of an acid catalyst, such as a Lewis acid, as for example boron trifluoride, which compound may be conveniently used in the form of its complex with diethyl ether, otherwise known as boron trifluoride etherate.

The process is also preferably carried out in presence of an inert organic solvent medium, as for example, chloroform or dichloromethane. The temperature at which the process of the invention is effected is not critical, but it will evidently be advantageous to use as low a temperature as is consistent with a reasonable yield, in order to avoid contamination of the desired product with byproducts which could result from decomposition and/or side reactions at higher temperatures. It is found that when conducting the process of the invention in presence of a catalyst such as boron trifluoride etherate, a temperature within the range of about 20° to 30° C. is suitable, but higher or lower temperatures may of course be used; a reaction temperature of about 25° C. is preferred. In order also to avoid undesirable contamination due to oxidation, it is preferable to conduct the reaction in an atmosphere of inert gas such as nitrogen.

In a particular embodiment of the invention, therefore, a process for preparing the compounds of formula (I) comprises reacting 3-hydroxy-3-mercaptopropyl-quinuclidine with a carbonyl compound of formula $R^1$—CO—$R^2$, in an atmosphere of ntrogen, at a temperature in the range of about 20° to about 30° C., preferably at about 25° C., in the presence of boron trifluoride etherate as catalyst and in dichloromethane or/and chloroform as the solvent medium, and isolating the desired product from the reaction mixture.

In this particular embodiment of the process, it is preferred that the reaction ingredients are first mixed in an atmosphere of nitrogen at a temperature between about −10° and +20° C., e.g. at about 0° C. and the mixture thus obtained is permitted to rise to the reaction temperature.

The invention further provides a process for preparing the compound of formula (I) which is 3hydroxy-3-mercaptomethylquinuclidine, wherein the epoxide of 3-methylenequinuclidine is reacted with hydrogen sulfide; in one alternative this reaction may be carried out in the presence of a base such as sodium hydroxide, preferably in an aqueous medium, while in another alternative the reactin with hydrogen sulfide may be effected e.g. in DMSO+(chloroform and/or toluene) as solvent medium. The epoxide may itself be prepared by reacting quinuclidin-3-one with dimethylsulfoxonium methylide.

The preparative processes of the present invention, including the processes by which relevant starting materials are prepared, are illustrated in a preferred embodiment, in the following reaction scheme:

REACTION SCHEME

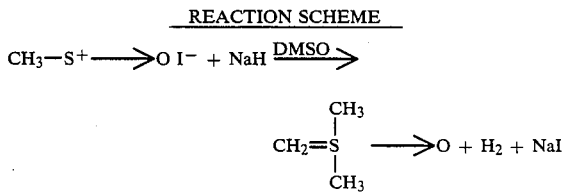

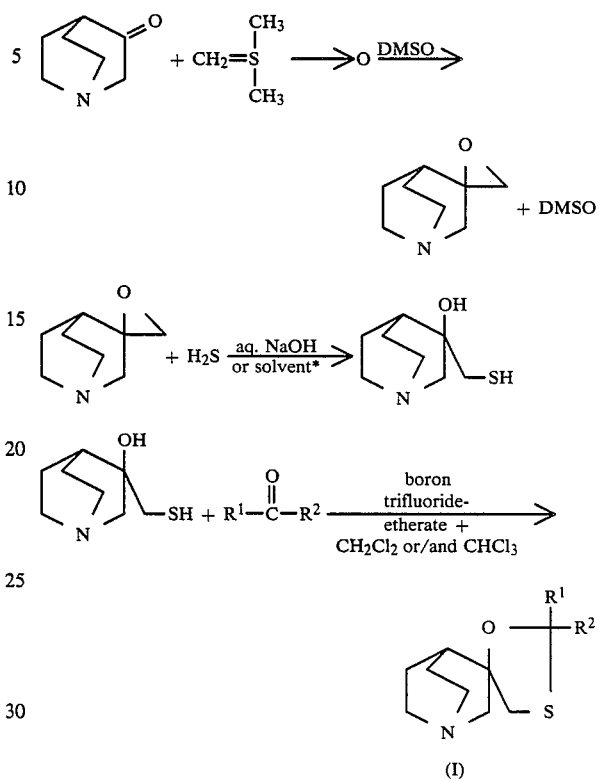

(DMSO = dimethylsulfoxide)
*DMSO + (chloroform and/or toluene)

The spiro-compounds of formula (I) have central nervous system activity. Thus, for example, the compound (Ia) is a muscarinic agonist with a high specificity for the central nervous system. Due to its pharmacological properties, it can be used to activate central cholinergic functions under conditions where the cholinergic system is hypofunctional. It can accordingly be utilized for the treatment of conditions such as senile dementia of Alzheimer's type(SDAT), tardive dyskinesia, Pick's disease, Huntington's chorea, Gilles de la Tourette disease, Friedrich's ataxia, and Down's syndrome, because all of these are disturbances in which a central cholinergic hypofunction has been implicated to some extent. This compound appears to be of especial value for the treatment of SDAT, since it is effective in reversing memory disorders due to AF64A-induced cholinotoxicity in a suitable animal model for this disease. In particular, the geometrical isomer of compound (Ia), of which the HCl salt has the relatively lower melting-point (the cis-isomer), and which has been assigned the code number AF102B, reverses memory impairments in AF64A-treated rats as shown in a passive avoidance test, in the Morris Swimming Maze (see Morris, Learning and Motivation, 12: 239–61, 1978) and in the 8-Arm Radial Maze. [The other geometrical isomer of the compound (Ia), of which the HCl salt has the relatively higher melting-point (the trans-isomer, has been assigned the code number AF102A]. In this context, AF64A (3 nmol/2 μl/side, icv) induces marked cognitive impairments in a step-through passive avoidance test, in the Morris Swimming Maze and in the 8-Arm Radial Maze, when the rats are analyzed four to eight weeks following treatment (Brandeis etal, in Alzheimer's and Parkinson's Disease: Strategies in Research and Development, eds. Fisher et al, Plenum Press, N.Y., in press; Fisher and Hanin, Ann. Rev. Pharmacol. Toxicol., 26: 161-81 (1986).

The beneficial affects of AF102B in the passive avoidance and Morris Swimming Maze tests occur at low doses (0.1–1 mg./kg., ip or 1 mg./kg., po) and the therapeutic index is 78–780 and 22 156, respectively. This therapeutic index is wider than that found for physostigmine (5–17). Moreover, the slope of the acute toxicity curve is very steep, and no overt behavioral effects including parasympathomimetic effects, such as salivation or tremors, were detected up to the lethal dose. In this reagard, the compound is superior to well known muscarinic agonists including arecoline and oxotremorine, in which such adverse side-effects complicate their possible use in SDAT therapy. In addition, AF102B has a long duration of action in the above-mentioned memory tests.

Interestingly, the compound is well absorbed into the blood following per os administration since its onset of action is short, i.e. around 10–15 minutes. This is evident in the following pharmacological tests: analgesia, hypothermia, and lethal dose level, induced by AF102B.

When compared to physostigmine (0.1 mg./kg.,ip), AF102B (5 mg./kg.,ip) is superior since it improves AF64A-induced memory impairments in the 8-Arm Radial Maze, a test in which physostigmine failed under the same experimental conditions.

The lack of adverse side effects induced by Af102B is remarkable also in analgesia tests (in mice) and hypothermia tests (in rats), two pharmacological tests employed to evaluate central muscarinic activity. In these tests only high doses of the compound elicited any significant side effects. Such doses are at least 15–150 (i.p.) or 40 (p.o.) times higher than those required to reverse AF64A-induced memory impairments in rats in the passive avoidance test.

Biochemical studies revealed that AF102B is a specific centrally active muscarinic M1-type agonist and is the first such compound known to the inventors. This selectivity became evident when AF102B was evaluated in the displacement of [$^3$H]-pirenzepine, [$^3$H]-PNZ, (an M1-specific antagonist) versus [$^3$H]-quiniclidinyl benzilate, [$^3$H]-QNB (an M1 and M2 antagonist) from rat brain homogenates. [Trends in Pharmacol. Sci. (Suppl), Jan 1984].

In this regard, it was found that M1-type muscarinic receptors found mainly in the cortex and hippocampus are relatively unchanged in SDAT (Mash et al, Science 228: 115–117, 1985). These two brain areas in SDAT show the most profound presynoptic cholinergic hypofunctions, and histological abnormalities, and are mainly associated with cognitive dysfunctions reported in SDAT.

The specificity of AF102B to muscarinic receptors in general and M1-receptors in particular, is also evident from lack of any significant activity on high-affinity choline transport (from rat brain synoptosomes) or choline acetyltranferase activity (from rat brain homogenates).

The M1-agonist type of activity of AF102B can be responsible at least in part for the high selectivity of AF102B both in vitro and in vivo (especially in reversal of cognitive impairments induced by AF64A).

Mutagenicity studies on AF102B in vitro have revealed that the compound is not mutagenic up to high concentrations. These data taken together with the large therapeutic index of this compound make it a potential drug for treatment of SDAT patients.

In SDAT patients, AF102B can be used in combination with anticholinesterase inhibitors such as physostigmine or tetrahydroaminoacridine; in combination with acetylcholine precursors such as choline or lecithin; in addition to "nootropic" drugs such as piracetam, aniracetam, oxiracetam or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin.

AF102B, with or without the aforementioned other active substances, can be administered for example, by way of injection in a suitable diluent or carrier, per os, rectally in the form of suppositories, by way of insufflation, by infusion or transdermally in a suitable vehicle with or without physostigmine, for example by using the device which is the subject of Israel patent application No. 72684 (vide infra). This compound may also be used in disturbances where cholinergic underactivity is induced by drugs.

The compound (Ia), in the form of either geometrical isomer, or a mixture of such isomers, is also of use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyrylcholinesterase. This compound may also be used for the treatment of peripheral cholinergic disorders such as myasthenia gravis, urinary bladder dysfunctions, Adi's disease and Eaton-Lambret disease.

When in the spiro-compounds of formula (I), $R^1$ and/or $R^2$ are propyl or higher alkyl groups, cyclopentyl, cyclohexyl, aryl, diarylmethylol, or alkyl substituted by aryl, the nature of the pharmacological activity of these compounds is changing, insofar as while they still possess central nervous system activity, this activity is now becoming anticholinergic instead of cholinergic. Such anticholinergic compounds can be used to treat disorders due to cholinergic hyperfunction, whether this be spontaneous or drug-induced. These compounds may accordingly be used in the treatment of Parkinson's disease, pseudo-Parkinson's disease, mental depression and as adjuncts of surgery instead of (e.g.) atropine or scopolamine. They also be used in opthalmology when prolonged mydriasis is required for diagnostic and therapeutical purposes.

Where the term "pharmaceutical composition" is used in the specification and claims, this is to be understood in the sense that it may be suitable for human and/or veterinary treatment.

According to a further aspect of the invention, therefore, there is provided a pharmaceutical composition which comprises a quinuclidine derivative of formula (I) or a pharmaceutically compatible acid addition salt thereof, together with an inert carrier or diluent. The term "pharmaceutically compatible acid addition salt" as used herein refers to a combination of said quinuclidine derivative with relatively non-toxic inorganic or organic acids. Illustrative only of suitable acids are sulfuric, phosphoric, hydrochloric, hydrobromic, hydriodic, sulfamic, methanesulfonic, benzenesulfonic, para-toluenesulfonic, acetic, lactic, succinic, maleic, tartaric, citric, gluconic, ascorbic, benzoic and cinnamic acids. Suitable pharmaceutical carriers and diluents, which comprise both solids and liquids, may, by way of example only, be selected from corn starch, lactose, calcium phosphate, stearic acid, polyethylene glycol, water, sesame seed oil, peanut oil, propylene glycol, and so forth. This composition may be in a form suitable for oral, rectal or parenteral administration, or for administration by insufflation, or in particular it may be in a form suitable for transdermal administration, and in any event the composition may be in unit dosage form. Exemplary compositions may take the form of tablets, powder, granules, capsules, suspensions, solutions, suppositories, elixirs, ointments and the like.

The pharmaceutical composition may contain as the spiro-compound of formula (I), for example, the compound identified herein as (Ia), and in particular the geometrical isomer(AF102B) of which the hydrochloric acid salt has the relatively lower melting-point. For the reasons noted hereinbefore, such a composition may contain as a further ingredient or ingredients, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

Alternatively, the pharmaceutical composition may contain as the spiro-compound of formula (I), such a compound in which one of $R^1$ and $R^2$ is selected from the group consisting of alkyl containing three or more carbon atoms, cyclopentyl, cyclohexyl, aryl and alkyl substituted by aryl, and the other of $R^1$ and $R^2$ is as previously defined, and in particular this compound may be one of those identified herein as (Ib) and (Ic).

When the pharmaceutical composition is to be administered transdermally, it is preferred to utilize the drug delivery system according to Israel patent application No. 72684, although transdermal administration in accordance with the invention is not of course limited to this system. Thus, there is also provided in accordance with the invention, a pharmaceutical composition for transdermal administration, which comprises a compound of formula (I) or a pharmaceutically compatible acid addition salt thereof, as well as a low molecular weight fatty acid.

The invention also relates to a method for treating diseases of the central nervous system in mammals (i.e. in humans or in non-human mammals), which comprises administering to the mammal a compound of formula (I) or a pharmaceutically compatible acid addition salt thereof, which compound may of course be administered in the form of the pharmaceutical composition described hereinbefore. This method for treating diseases of the central nervous system in mammals may of course also be applied by using the drug delivery system of the Israel Patent Application which has been described above.

More specifically, the method for treating diseases of the central nervous system in mammals, in accordance with the present invention, may be used for treating diseases due to a deficiency in the central cholinergic system in mammals, in which case the method comprises administering to the mammal the compound (Ia), including the geometrical isomers, enantiomers, diastereoisomers, racemates and/or acid addition salts thereof; the compound (Ia) may be administered in the form of a pharmaceutical compositions, which may be optionally supported for transdermal administration in the form of the device of Israel patent application No. 72684, as has already been described hereinbefore.

In another aspect of the present invention, the method for treating diseases of the central nervous system in mammals may be used for treating diseases due to a cholinergic hyperfunction in mammals, in which case the method comprises administering to the mammal the spiro-compound of formula (I) in which one of $R^1$ and $R^2$ is selected from the group consisting of alkyl containing three or more carbon atoms, cyclopentyl, cyclohexyl, aryl and alkyl substituted by aryl, and the other of $R^1$ and $R^2$ is as previously defined, as for example, either of the compounds (Ib) and (Ic), including the geometrical isomers, enantiomers, diastereoisomers, racemates and/or acid addition salts of such spiro-compounds of formula (I); these compounds may be administered in the form of pharmaceutical compositions, which may be optionally supported for transdermal administration in the form of the device of Israel patent application No. 72684, as has already been described hereinbefore.

In yet a further aspect of the present invention, the method for treating diseases of the central nervous system may be used for treating senile dementia of Alzheimer's type in humans, in which case the method comprises administering to a patient the geometrical isomer of compound (Ia), the hydrochloric acid salt of which has the relatively lower melting-point, including the enantiomers, diasteroisomers, racemates and/or acid addition salts of this geometrical isomer; the geometrical isomer of the compound (Ia) may be administered in the form of pharmaceutical compositions, which may be optionally supported for transdermal administration in the form of the device of Israel patent application No. 72684, as has already been described hereinbefore. Optionally, there may be administered in general, together with the aforementioned geometrical isomer of the compound (Ia), one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin. In the case of transdermal administration, however, the additional ingredient is preferably one or more compounds selected from the group consisting of physostigmine, tetrahydroaminoacridine, 4-aminopyridine and 3,4-diaminopyridine.

For the purpose of definition, it is intended that the expression "method for the treatment of diseases of the central nervous system", and like expressions, throughout the specification and claims, be taken to include a method for the prevention of drug-induced diseases of the central nervous system.

As regards suitable dosages for the administration of the compounds of the invention, some indication has been obtained from the biological tests, the results and other details of which are recorded infra. It would at present appear that for administration per os it is unlikely that a single dosage of more than about 60 mg./kg. or less than about 0.1 mg./kg. body weight would be suitable, and that a single dosage in the range of about 0.5 to about 10 mg./kg., especially in the range of about 1 to about 5 mg./kg., is to be preferred. For parenteral administration (which includes, for example, intramuscular, intravenous and subcutaneous administration) it at present appears to be unlikely that a single dosage of more than about 40 mg./kg. or less than about 0.01 mg./kg. body weight would be suitable, and that a single dosage in the range of about 0.05 to about 5 mg./kg., especially in the range of about 0.1 to about 2 mg./kg., is to be preferred. In prescribing a particular form and rate of administration, the physician will of course take into consideration the usual factors such as the severity of the symptoms, the physical circumstances of the patient, and so forth.

Taking into account the usual weight ranges of patients, the foregoing dosage ranges, and the possiblity that it may be desirable to administer multiple rather than single doses, pharmaceutical compositions in accordance with the invention which are adapted for oral or parenteral administration, may contain the active ingredient (and especially the compound identified herein by the code number AF102B), for example, in an amount in the range of about 0.5 to about 500 mg., preferably about 5 to about 100 mg., more preferably in the range of about 10 to about 50 mg.

BRIEF DESCRIPTION OF THE DRAWINGS

FIG. 1 shows the NMR(250 MHz) spectrum of 3-hydroxy-3-mercaptomethylquinuclidine.

FIG. 2 shows the NMR(250 MHz) spectrum of cis:-trans (Ia)-HCl salt [AF102].

DETAILED DESCRIPTION OF THE INVENTION

Figure 3:
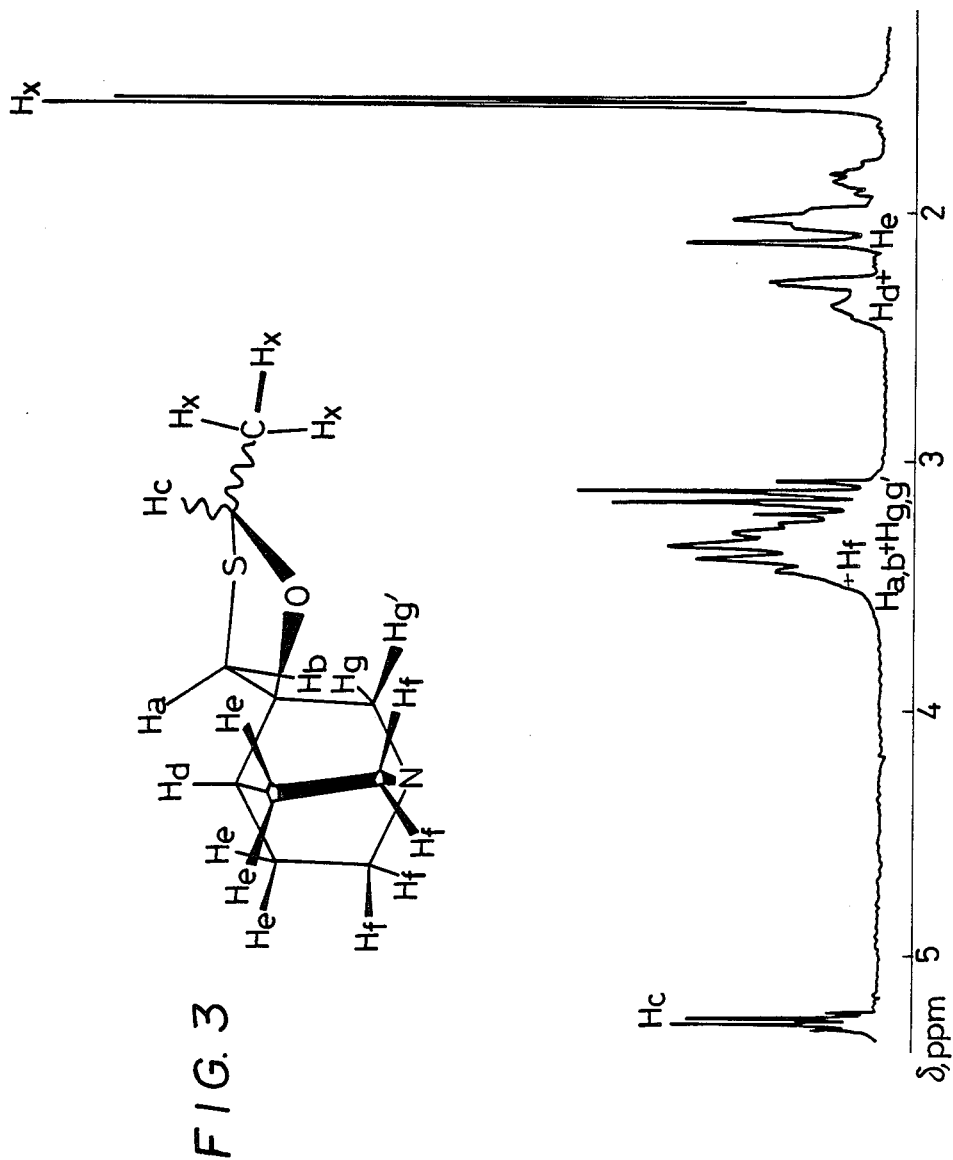
FIG. 3 shows the NMR(250 MHz) spectrum of the geometrical isomer of (Ia)-HCl salt identified as AF102A.

The invention will now be described in further detail with regard to Examples for the preparation of the compounds of the invention, and biological testing of the spiro-compounds of the invention.

EXAMPLE I

Preparation of 2-methylspiro(1,3-oxathiolane-5',3)quinuclidine. [AF102 (cis:trans); AF102A and AF102B]

(a) Epoxide of 3-methylenequinuclidine.

(i) In a 3 l. three-necked flask fitted with a mechanical stirrer and thermometer, was placed sodium hydride (42 g., 0.88 mole, as a 50% dispersion in oil) and 300 ml. petroleum ether (30°–60°). The suspension was stirred, the hydride allowed to settle, the petroleum ether decanted, and with stirring 1200 ml. of dry DMSO was added, followed by trimethyloxosulfonium iodide (214 g., 0.97 mole), which was added portionwise over a period of 15 minutes, and stirring was then continued for an additional 30 minutes. The reaction flask was equipped with a sealed pressure-compensating dropping funnel containing quinuclidin-3-one (100 g., 0.8 mole) dissolved in 300 ml. dry DMSO. This solution was then added to the reaction mixture over a 15 minute period. After stirring for 15 minutes, the reaction mixture was heated to 50° C. for 2 hours, poured into 1 l. of cold water and the mixture extracted with $3 \times 500$ ml. portions of benzene. The combined extracts were washed with 100 ml. of saturated aqueous salt solution, dried over anhydrous sodium sulfate, and the solvent evaporated. The oily residue was dissolved in ether and precipitated as the salt with hydrochloric acid by addition of ether saturated with gaseous HCl. The epoxide product was separated by filtration, washed with ether and dried to give 100 g. product which was sufficiently pure to use for the next step. $R_f 0.3$ on neutral alumina (ethyl acetate); $M^+ = 139$ (mass spectra determinations on a VG 7035 instrument); HCl salt has m.p. 200.7°–202° C.

(ii) In an alternative synthesis that can also be scaled up, 2.2 kg. of quinuclidin-3-one (HCl salt) were added to a 5 liter flask and 2 liters of tap water were then added followed by 1 kg of NaOH. The mixture was mechanically stirred at 50° C. till the solids dissolved. Under these conditions 3 phases are obtained, two upper phases (liquids) and a lower phase (solid).

The mixture is kept at 60° C. The upper phase is added to 1 liter of toluene. The two lower phases including the solid phase were filtered. The solid was mashed in 1 liter of toluene that was also used to mash the water phase. The toluene phases were combined, treated with powdered charcoal to remove color (and impurities), dried over MgSO$_4$ and filtered to yield 3.3 kg. of product inclusive of toluene; a sample of 215 g. of solution was evaporated to obtain 106 g. of quinuclidin-3-one (free base) as a white solid, which was sufficiently pure for practical purposes. (Therefore, under these conditions at least a 88–90% extraction yield can be obtained). The toluene solution is dried by azeotropic distillation; the dried solution can be used for the next step.

In a 3 liter three-necked flask were introduced quinuclidin-3-one (193 g., 1.54 mole) in azeotropically-dried toluene solution (weight of solution 563 g), trimethylsulfoxonium iodide (380 g., 1.72 mole) and NaH 55-60% dispersion in paraffin oil (70 g., 1.68 mole) and then the mixture was mechanically stirred. A weak evolution of $H_2$ followed that ceased after 2-3 minutes.

The reaction flask was cooled in cold water and DMSO (0.5 l., dried 1 month on molecular sieves) was added dropwise; 100 ml. were added in one step and the remainder added dropwise during 1.5 hours with stirring and cooling the reaction mixture between 10° and 30° C. The reaction mixture was then heated to 50°-55° C. for 1 hour till reaction was complete, as determined by TLC on neutral alumina (methanol:dichloromethane, 5:95). The reaction mixture was poured into 1 liter of cold water and the mixture was extracted with 0.5 l. portions of chloroform. In each extraction the interphase was removed by filtration; 2.4 liters of organic phase were collected and dried over 160 g. of $MgSO_4$. The NMR (250 MHz) shows about 120 ml. of DMSO (calculation based on the ratio DMSO/Toluene). Thus, 80% of DMSO was removed by this treatment. TLC shows the product is slightly impure due to DMSO and other compound(s). This solution was partially evaporated to 1900 ml. and kept at 0°-4° C. for 5 days without change. This solution is sufficiently pure to use for the next step.

(b) 3-hydroxy-3-mercaptomethylquinuclidine.

Figure 5:
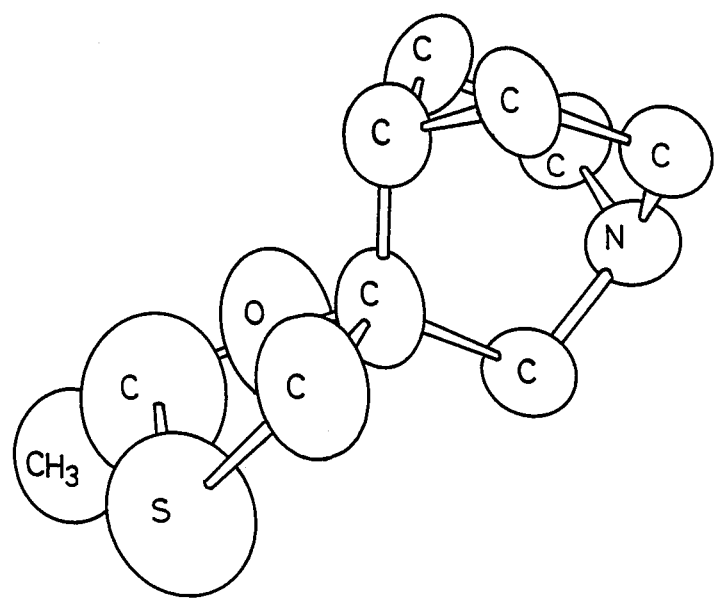
FIG. 5 depicts the structure of AF102B, as determined by X-ray crystallography of its HCl salt, showing that AF102B is the cis-isomer.
Figure 6:
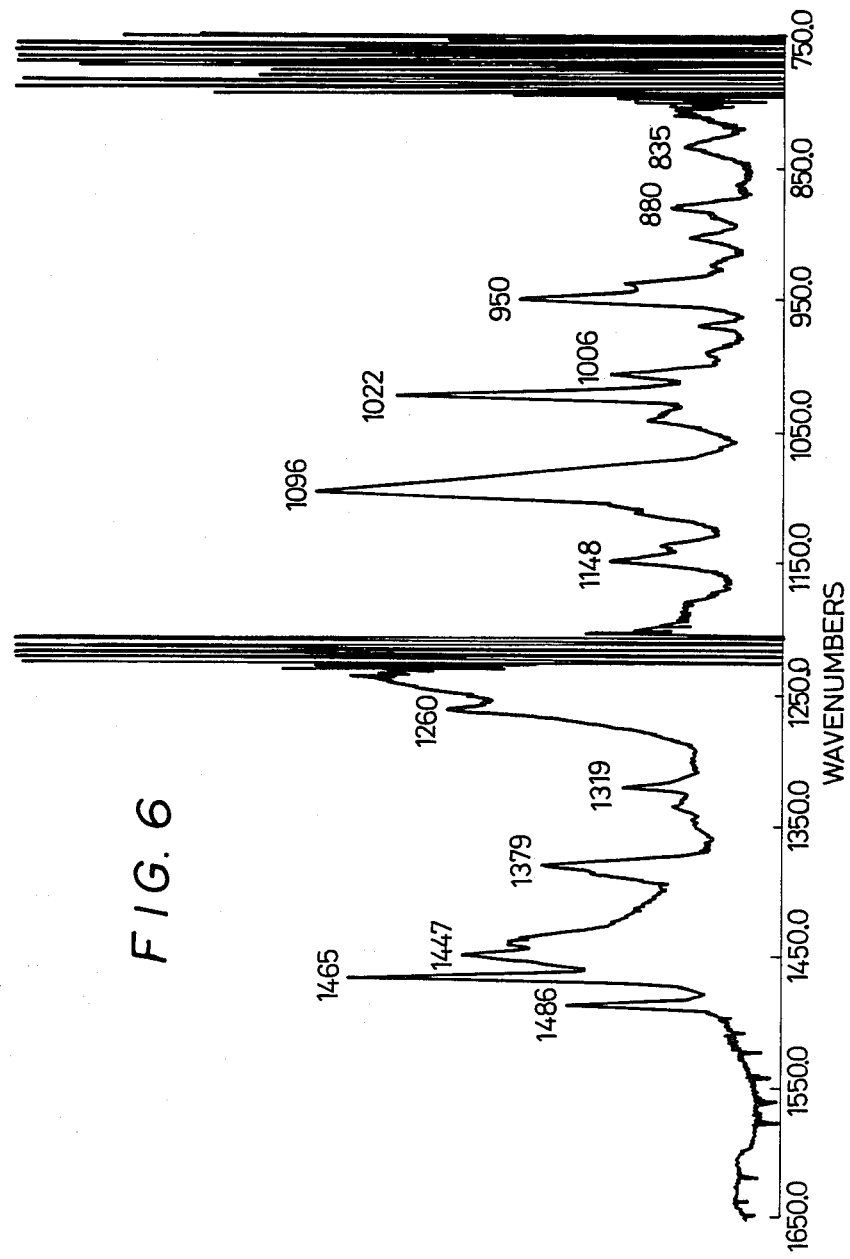
FIG. 6 shows the IR spectrum (on Nicolet 20XB FTIR) of the geometrical isomer of (Ia)-HCl salt identified as AF102A.
Figure 7:
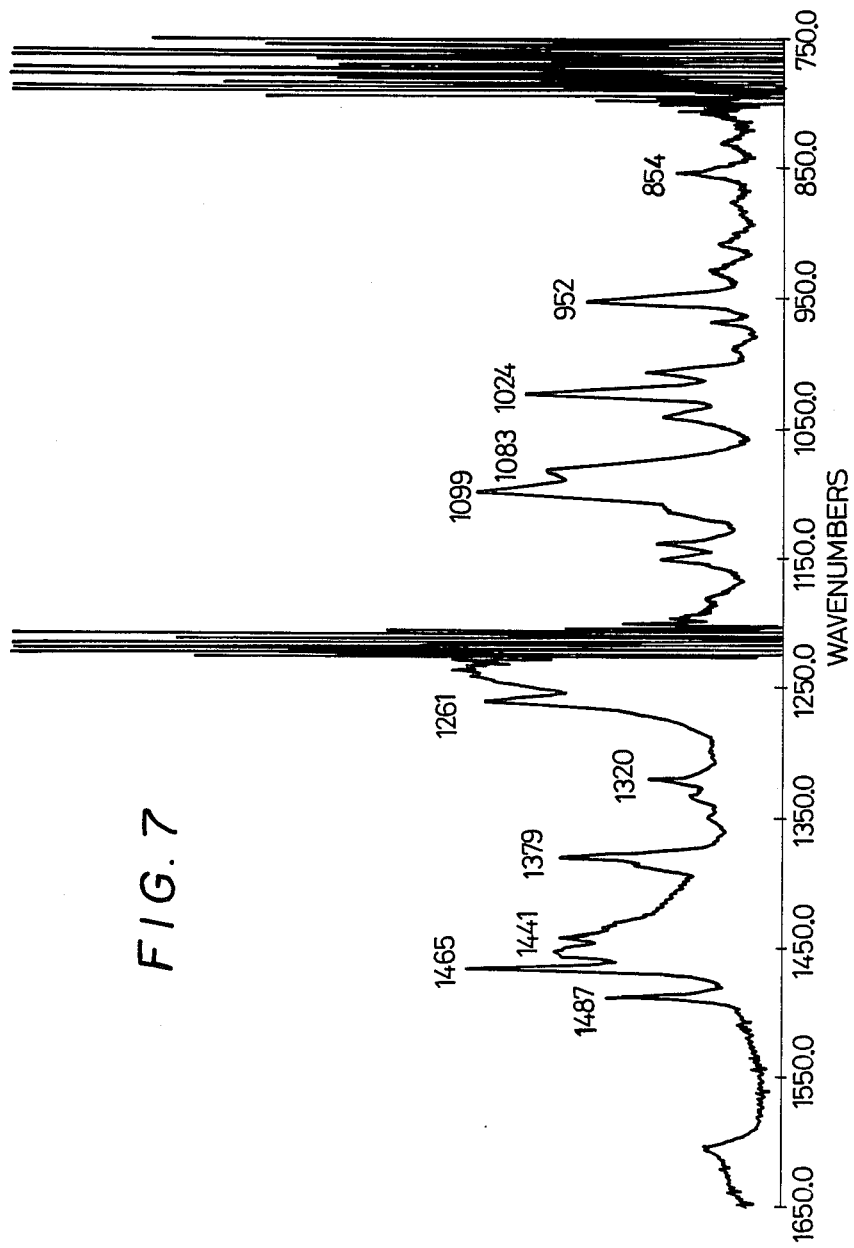
FIG. 7 shows the IR spectrum of the geometrical isomer of (Ia)-HCl salt identified as AF102B.

(i) In a 1 l. three-necked flask equipped with a magnetic stirrer, an inlet and an outlet for hydrogen sulfide and a thermometer, were placed 80 g. NaOH and 390 ml. water. The solution was cooled in an ice-bath and gaseous hydrogen sulfide was passed into the stirred solution until it began to bubble out. The product of step (a) (80 g., 0.46 mole) was then added, and stirring was continued for 15 minutes. The reaction mixture was heated to 45° C. for 2.5 hours under a slow stream of hydrogen sulfide. The solution was cooled to 0° C., and 10N HCl was carefully added to bring the pH to 8; the aqueous solution was then extracted with chloroform (6×300 ml.). The combined extracts were dried over anhydrous sodium sulfate and evaporated to dryness. The resulting solid was dried over phosphorus pentoxide in a dessicator to give 32.9 g. of crude product. After purification (TLC, neutral alumina, 10:1 dichloromethane+methanol) $R_f$ 0.5; $M^+$ (see FIG. 5)=173; base peak=140; NMR (see FIG. 1) peak at 250 MHz(CDCl$_3$) δ 2.8→double doublet, —CH$_2$—SH, AB-type spectrum; IR $\nu_{max}$ 2900-3300 cm.$^{-1}$ (broad). The compound was used for the next step without any further purification.

(ii) In an alternative method, the chloroform solution of step (a) (ii), above, (1520 g.) was introduced into a 3 l. three-necked flask equipped with a mechanical stirrer, a H$_2$S inlet and two traps with concentrated NaOH solution to trap excess H$_2$S. The reaction mixture was kept at 25±5° C. and H$_2$S was bubbled into it for 8.5 hours, after which it was allowed to stand overnight. The next day, H$_2$S was again bubbled in for 5 more hours, when the reaction was complete (TLC) and could be used for the next step without any further purification.

(c) 2-methylspiro(1,3-oxathiolan-5,3')quinuclidine.-[AF102 cis:trans]

(i) In a 0.5 l. three-necked flask equipped with a magnetic stirrer, an inlet and an outlet for nitrogen gas and a thermometer, were placed the product of step (b) (i) (32 g., 0.18 mole), 200 ml. dichloromethane (dried over molecular sieves) and freshly distilled acetaldehyde (110 ml., 1.97 mole). The solution was cooled in an ice-bath under nitrogen gas, and boron trifluoride etherate (60 ml., 0.40 mole) was added over a period of 30 minutes. The mixture was stirred three hours at 25° C., cooled to 0° C., and then treated with 10% aqueous NaOH solution until it was alkaline to litmus. The alkaline solution was extracted with chloroform (4×400 ml.), and the combined extracts were dried over anhydrous sodium sulfate and evaporated. The oily residue was dissolved in ether and precipitated by addition of gaseous HCl. The product hydrochloride was separated by filtration, washed with ether and dried, to give 26.5 g. (yield: 62%), as a mixture of two geometric isomers in a ratio of 0.8-1.2:1. $R_f$(TLC, neutral alumina, chloroform) 0.7; $IR_{max}$ (using a Perkin-Elmer 457 grating infrared spectrophotometer) C-O 1200-1250, 1150 cm.$^{-1}$; $M^+$=199; high resolution molecular weight determination: calc. for $C_{10}H_{17}NOS$: 199.1020, found: 199.1017.

NMR of the HCl salt is shown in FIG. 2. Resolution of the spectrum enables the existence of both isomers to be seen. The location of the —S— in the oxothiolane ring is evident from the chemical shifts of the respective Ha and Hb protons. These protons in the isomeric mixture and also in each of the isomers appear at higher field than their possible chemical shifts if they had been attached to —O— as in the analogous 1,3-dioxolane structure. The product can be recrystallized from ethyl acetate (600 ml. per g.) or from acetone (220 ml. per g.).

The isomeric mixture of hydrochlorides can be separated into its components by fractional recrystallization in redistilled dry acetone. Melting points as well as NMR spectra of 250 MHz can be used as an indication of purity for each isomer. Such a separation will be described in step (d).

(ii) In an alternative method, AF102 in free base form is prepared directly from the solution of crude thioalcolhol. Thus, such a solution from step (c) (ii) containing 240 g. of thioalcolhol (1.38 mole) was added to a 5 liter 3-necked flask, cooled in cold water to 10° C. and then acetaldehyde (680 ml.; freshly distilled on para-toluene sulfonic acid) was added during 30 mins. and the temperature was kept at 20±5° C. during this time. The solution was then cooled to 15° C. and stirred for another 30 mins. BF$_3$-etherate (450 ml) was added dropwise during 30 mins. and the solution was kept ar 20±5° C. and stirred for an additional 30 mins. A solution of 20% NaOH (1 liter) was added dropwise and the reaction temperature was kept at 20±5° C. during this addition.

The mixture was filtered and the water solution was extracted with 1 liter of chloroform. The chloroform extracts were combined, dried over MgSO$_4$ and evaporated. The oil obtained could be distilled at ca. 90° C./1 mm. Hg to obtain AF102 (cis:trans), or alternatively diluted with 2.5 l. toluene. In the latter case, 5-10 g. of solid which deposited on the walls of the flask were removed and HCl (gaseous) was bubbled into the toluene solution till the organic solution was acidic to pH paper; the solid cake was filtered off, washed with toluene, dissolved in ¾ l. isopropanol at 50°-60° C. and filtered to remove insoluble impurities. The filtrate was evaporated with the addition of 1 l. toluene to obtain 168 g. of crude product AF102 (cis:trans) (HCl) with some slight impurity as shown by TLC. This product (crude yield 51%) can be purified further as described below in step (d).

(d) Separation of AF102 into its components AF102A and AF102B.

A 1:1 isomeric mixture of hydrochlorides was crystallized from 4.7 l. of redistilled dry acetone. The product which precipitated was crystallized again (see Table), to yield after four crystallizations 1.9 g. of pure AF102A, m.p. 240°-242° C. Concentration of the mother liquor (see Table) resulted in an oily product which was purified on an alumina column (as a free base, 1% methanol in dichloromethane) to give mainly (10:1) the isomer AF102B, m.p. 176°-179° C. as the HCl salt.

(dried over molecular sieves) and diphenylacetaldehyde (15 ml., 0.085 mole). The solution was cooled in an ice bath, and kept under nitrogen while distilled boron trifluoride etherate (20 ml., 0.13 mole) was added over a period of 30 minutes. The mixture was stirred two hours at 25° C., cooled to 0° C. and then treated with 10% aqueous sodium hydroxide until the solution was alkaline to litmus. The basic solution was extracted with benzene (4×400 ml.), and the combined extracts were dried over anhydrous sodium sulfate and evaporated. The oily residue was dissolved in ether and precipitated as the hydrochloric acid salt by addition of gaseous HCl. The product was further purified on a neutral alumina column as free base using 1:10 petroleum

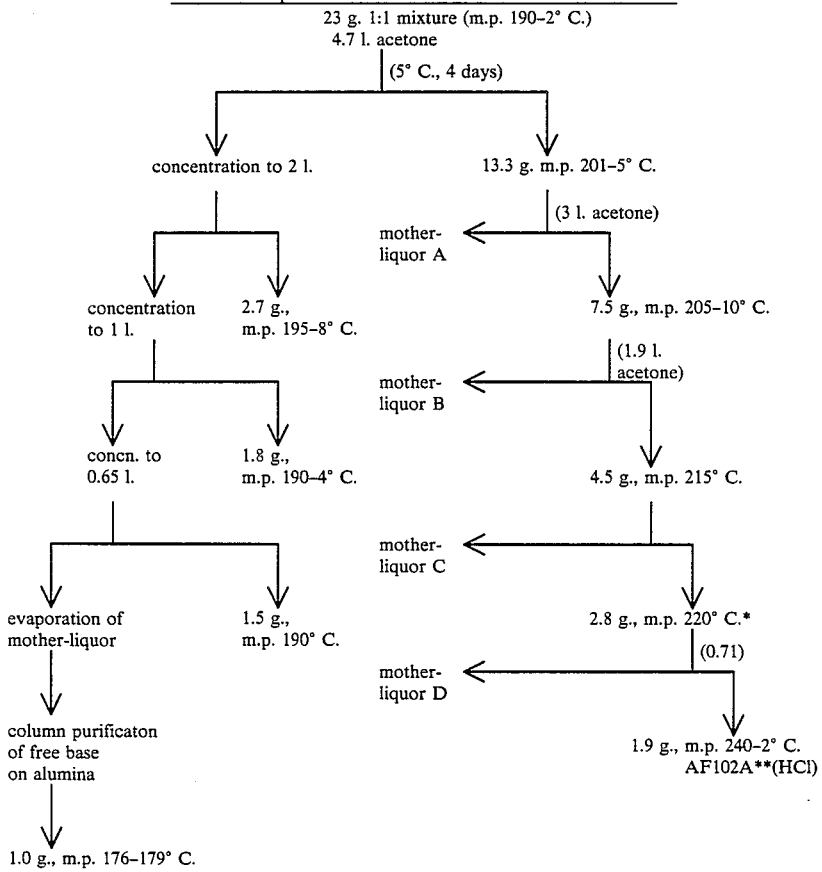

TABLE: Separation of AF102A and AF102B as HCl salts.

1.0 g., m.p. 176-179° C.
AF102B***(precipitated as HCl salt)
*isomer ratio 10:1
**pure isomer (NMR)
***isomer ratio about 1:10 (NMR)

AF102A(HCl): NMR (see FIG. 3), 250 MHz (CDCl$_3$) δ 5.24 (quartet, peak of $R^1$=H, which is a quartet since it is coupled to $R^2$=CH$_3$).

Figure 4:
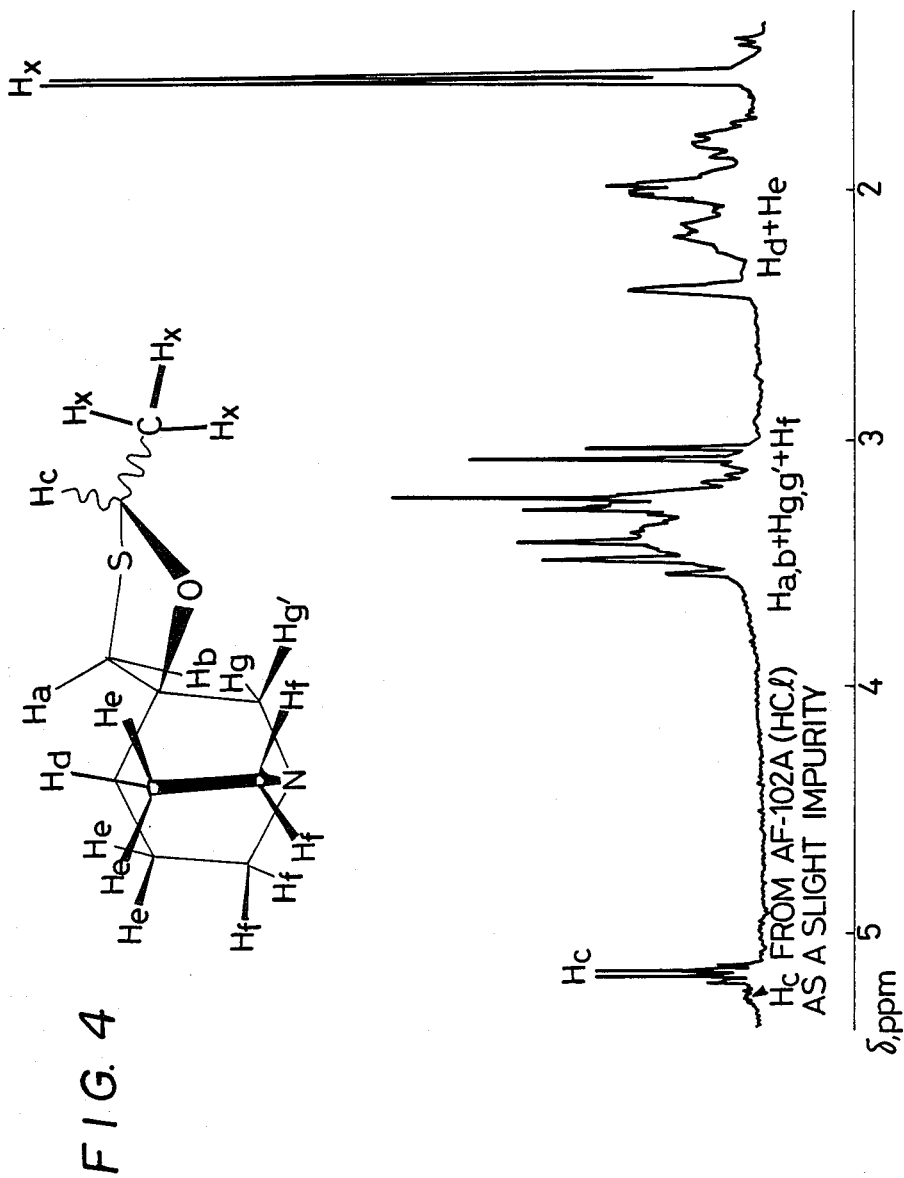
FIG. 4 shows the NMR(250 MHz) spectrum of the geometrical isomer of (Ia)-HCl salt identified as AF102B.

AF102B(HCl): NMR (FIG. 4), 250 MHz (CDCl$_3$) δ 5.17 (quartet, peak of $R^2$=H, which is a quartet since it is coupled to $R^1$=CH$_3$).

EXAMPLE II

Preparation of 2-diphenylmethylspiro(1,3-oxathiolane-5,3')quinuclidine

In a 100 ml. three-necked flask equipped with a magnetic stirrer, an inlet and outlet for nitrogen and a thermometer, were placed 3-hydroxy-3-mercaptomethylquinuclidine (8 g., 0.045 mole), 40 ml. dichloromethane ether(40°-60°)/ethyl acetate as the eluent. Under these conditions, 2 g. of the title compound were isolated. $M^+$ =351.

EXAMPLE III 2-methyl-2-phenylspiro(1,3-oxathiolane-5,3')quinuclidine

This compound was prepared by a similar method to Examples 1 and 2, by reacting acetophenone with 3-hydroxy-3-mercaptomethylquinuclidine. The yield was relatively low (10-20%). $M^+$ =275.

Various other compounds within the ambit of formula (I) can be prepared by the exemplified method by using the appropriate aldehyde $R^1$—CHO or ketone $R^1$—CO—$R^2$, where $R^1$ and $R^2$ are as defined with respect to formula (I).

As has already been mentioned, the spiro-compounds of formula (I), including their pharmaceutically compatible acid addition salts may be formulated, together with conventional pharmaceutical inert carriers, diluents, adjuvants and so forth, as pharmaceutical compositions, which may be in a form suitable for oral, rectal or parenteral administration, or for administration by insufflation, or they may be in a form suitable for transdermal administration, and in any event the composition may be in unit dosage form.

The spiro-compounds of formula (I), or such pharmaceutical compositions containing them, may be administered to humans, as well as to laboratory animals such as rodents, cats, dogs and monkeys, as for example by peripheral or intracerebral or intracerebroventricular injections (for animals), by infusion, through the skin, or per os. It is evident that the dosage and the route will need to be adjusted according to the specific biological use, and in particular according to the nature of the disease or disorder to be treated and its severity.

For the reasons which have already been noted hereinbefore, such pharmaceutical compositions may, in the case of (Ia), contain as an additional ingredient, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

As has also been previously mentioned in some detail above, when the pharmaceutical compositions are to be administered transdermally, it is preferred to utilize the drug delivery system according to Israel Patent Application No. 72684.

Biological Testing of the Spiro-Compounds of the Invention

For AF102A and AF102B the general toxicity profile was first established. This study phase was routinely divided into two parts, i.e. "dose range finding" and $LD_{50}$ determination. In the former, usually pairs of mice were administered widely spaced dosages and the animals were subsequently observed. The type, time of onset and duration of reactions to treatment were recorded. $LD_{50}$ determinations were based on the preliminary findings of the range-finding studies. Under conditions of this study, the test material solutions were administered to at least five dose-level groups of at least five animals of the same sex per group and at geometrically-spaced dosages. On the basis of mortality, the $LD_{50}$ value and 95% confidence interval (C.I.) were calculated according to Weil's method (Weil, Biometrics, 8: 249-283, 1952).

| AF102A |  |
|---|---|
| (a) $LD_{50}$ mice; oral administration. | |
| Test conditions - male mice, 20-24 g. | |
| - N = 5/group | |
| - constant volume-dosage of 20 ml./kg. | |
| Dose (mg./kg. per os) | Mortality (number dead/number in group) |
| 160 | 5/5 |
| 139 | 5/5 |
| 120 | 4/5 |
| 104 | 2/5 |
| 90 | 2/5 |
| 78 | 0/5 |

$LD_{50}$ (95% C.I.) = 102 (89-117) mg./kg.

| -continued |  |
|---|---|
| (b) $LD_{50}$ mice; intravenous administration. | |
| Test conditions - male mice, 20-24 g. | |
| - N = 6/group | |
| - variable volume-dosage of 9.0-11.5 ml./kg. | |
| Dose (mg./kg. i.v.) | Mortality (number dead/number in group) |
| 45.0 | 6/6 |
| 42.5 | 4/6 |
| 40.0 | 2/6 |
| 37.9 | 3/6 |
| 36.0 | 2/6 |

$LD_{50}$ (95% C.I.) = 40.4 (35.5-45.9) mg./kg.

The relatively narrow ratio of about 1:2.5 between the $LD_{50}$ values of the i.v. and oral routes of administration suggests an efficient, rapid and apparently unaltered absorption of the test material by the enteric route.

(c) Signs observed.

Signs in reaction to treatment in mice and listed below were mostly confined to decedents, as survivors of treatment groups, administered respectively doses which caused only partial lethality, rarely demonstrated any of the reported affects in decedents. Undoubtedly, this finding points to a rather steep toxic-lethal slope of the test material.

Furthermore, there was essentially no obvious difference in effects observed between orally and intravenously treated animals, with the exception of time of onset, duration and time of death. Examination to assess pupillary changes were carried out only in surviving animals.

Signs are listed in order of their appearance:
slight transient decrease of spontaneous motor activity (only in orally treated animals)
severe tremors, particularly of head region (within 2-3 mins. or 10 secs. after oral or intravenous administration, respectively)
dyspnoea
convulsive seizures (clonic)
gasping, cyanosis
singular clonic-tonic convulsive seizure followed by death.

Death in mice to which were administered approximate $LD_{50}$ doses, occurred about 10-15 minutes. after oral administration and at about 30 secs. after intravenous injection, respectively. In surviving animals, transient partial analesic activity in response to tail-pricking could be detected. Likewise, even among survivors in which one of the above-described signs was shown, full recovery was extremely rapid. Another feature worthwhile mentioning is the finding of slight to moderate mydriasis after pupillary examination, in surviving animals of the intravenously-treated group.

It should be pointed out that none of the test animals exhibited effects considered characteristic of parasympatho- or cholinomimetic activity, i.e. continuous generalized tremors, salivation, lachrymation, or diarrhoea and miosis.

Rats to which were administered an oral dose of 100 mg./kg. showed the following:

10 mins. post-administration (p.a.), spontaneous motor activity was slightly reduced 15 mins. p.a. mydriasis, with pupillary size being about three times that seen in controls 20 mins. p.a., sudden onset of a brief clonic convulsive seizure which 5 mins. later changed into periodic head twitching and tremors 30 mins. p.a., animals appeared somnolent, accompanied by partial loss of righting reflex, dyspnoeic and cyanotic, with very slight salivation and lachrymation.

All of the above signs refer mostly to the one animal, out of the group of three, which was found dead at 40 mins. post-administration. In the remaining two rats, all of the above-displayed effects were much less in their relative intensity, and full recovery occurred after several hours.

| AF102B |  |
|---|---|
| (a) $LD_{50}$ mice; oral administration. | |
| Test conditions - male mice, 20-24 g. | |
| - N = 5/group | |
| - constant volume-dosage of 20 ml./kg. | |
| Dose (mg./kg. per os) | Mortality (number dead/number in group) |
| 113 | 4/5 |
| 101 | 3/5 |
| 90 | 2/5 |
| 80 | 2/5 |
| 71 | 0/5 |
| 64 | 0/5 |
| $LD_{50}$ (95% C.I.) = 92 (74–116) mg./kg. | |
| (b) $LD_{50}$ mice; intravenous administration. | |
| Test conditions - male mice, 20-24 g. | |
| - N = 6/group | |
| - variable volume-dosage of 9.0–11.5 ml./kg. | |
| Dose (mg. /kg. i.v.) | Mortality (number dead/number in group) |
| 39 | 6/6 |
| 37 | 6/6 |
| 35 | 5/6 |
| 33 | 1/6 |
| 31 | 3/6 |
| $LD_{50}$ (95% C.I.) = 33 (31–35) mg./kg. | |

The relatively narrow ratio of about 1:2.5 between the $LD_{50}$ values of the i.v. and oral routes of administration suggests an efficient, rapid and apparently unaltered absorption of the test material by the enteric route.

(c) Signs observed.

Inasmuch as both $LD_{50}$ values after i.v. and per os administration of AF102B were slightly lower than those obtained with AF102A, the general signs of reaction to treatment with the former were essentially similar to those reported for the latter, with the mere difference being confined to a slightly enhanced intensity in the case of AF102B.

It should be pointed out that, as with AF102A, none of the test animals exhibited effects considered characteristic of parasympatho- or cholinomimetic activity, i.e. continuous generalized tremors, salivation, lachrymation, or diarrhoea and miosis. This feature is in contrast to the cholinergically active compound of U.S. Pat. No. 4,104,397, namely cis-2-methylspiro(1,3-dioxolane-4,3')quinuclidine, hereinafter referred to under the code number AF30, which did exhibit such side effects.

Intraperitoneal Toxicity of AF102B in Rats

The acute intraperitoneal toxicity of AF102B (HCl) was investigated in five groups of five male and five female rats of the Charles River strain at dosages with the range 20.0–187.0 mg./kg. The test material was prepared at various concentrations in saline and was administered at a constant volume-dosage of 10 ml/kg. Mortality and signs of reaction to treatment were recorded during a 14-day period of observation. Early decedents and animals killed on day 15 were subjected to necropsy. It was found that deaths occurred at the three highest dose levels (61, 107, 187 mg./kg.), within twenty minutes after dosing.

The principal signs of reaction to treatment observed in both decedent and surviving animals were spastic and tonic convulsions, tremors, tachypnoea and dyspnoea, decreased motor activity, slight to very strong salivation and urination. In surviving animals all signs of reaction to treatment were resolved within two hours after dosing. Surviving animals generally made expected bodyweight gains over the study period. At necropsy the gross observations related to treatment were seen only in decedents. Congested blood vessels were observed in the brain of the high dosage group. No abnormalities were detected at necropsy of surviving animals. $LD_{50}$ (95% C.L.)=77.6 (60.1–100.2); slope =83°.

Acute Oral Toxicity of AF102B in Rats

The acute oral toxicity of AF102B (HCl) was investigated in four groups of five male and five female rats (Charles River CD strain). The test material was prepared at various concentrations in saline and was administered at a constant volume-sosage of 5 ml./kg. Dosages were selected according to the availability of the test material. Mortality and signs of reaction to treatment were recorded during a 14-day period. Early decedents and surviving animals were subjected to necropsy on Day 15. It was found that deaths occurred at all four dose-levels studied, within three hours 30 minutes after dosing.

The principal signs of reaction to treatment observed in both decedent and surviving animals were clonic convulsions, tremor, salivation, urogenital staining, diarrhoea and pigmented orbital secretion. In surviving animals, all clinical signs of reaction to treatment were resolved by twenty four hours after dosing. The main treatment-related finding of decedent animals at necropsy was salivation. Internally, a single case of haemorrhagic contents and occasional congested gastric mucosa was observed. Necropsy of surviving animals did not reveal any abnormalities. Surviving animals generally made expected bodyweight gains over the study period. The oral $LD_{50}$ of AF102B is estimated to be greater than 156 mg./kg.

| AF102B: Summary of Acute Toxicity in Studies of Mice and Rats (mg./kg.) ($LD_{50}$ + 95% Confidence Limits). | | | |
|---|---|---|---|
| Animal Specie | iv | ip | po |
| Mice | 33(31–35) | * | 92(74–116) |
| Rats | — | 77.6(60.1–100.2) | >156 |

*All mice died at 80 mg./kg., ip.

Analgesic (Antinociception) Activity in Mice of AF102B

The potential analgesic activity of the test material AF102-B was assessed in groups (n=5) of male and female mice, by use of two primary analgesic tests: Tail Clip and Phenylquinone Writhing. The test material was administered either by the oral or the intraperitoneal route at three different dose levels and the analgesic effect was compared with that of two reference compounds. In preliminary studies codeine phosphate (50 mg./kg., administered s.c. one hour before testing) and oxotremorine (either 0.1 mg./kg., administered p.o. one hour before testing, or 0.05 mg./kg., administered i.p. 30 minutes before testing), were selected as analgesic and cholinomimetic reference compounds, respectively. Under the conditions of this study, AF102-B exhibited antinociceptive activity only at dose levels greater than 20 mg./kg. p.o. and 10 mg./kg. i.p. This dose-dependent antinociceptive effect was not fully developed at 60 mg./kg. p.o. and 40 mg./kg. i.p., which were the highest non-lethal dose levels tested in this study and remained obviously weaker than those of codeine phosphate and oxotremorine.

Potential hypothermia-inducing activity of AF102B in rats

The potential hypothermia-inducing activity of the test material AF102B was assessed in groups of 8 male rats, comparatively with two reference materials. The rectal temperature was recorded before and at different times after administration of the test material, either by the oral or the intra-peritoneal route at three different dose levels. In preliminary studies chlorpromazine (10 mg./kg. administered i.p.) and oxotremorine (either 3.2 mg./kg., administered p.o. or 1.2 mg./kg. administered i.p.) were selected as neuroleptic and cholinomimetic reference material, respectively. Under the conditions of this study, AF102B exerted hypothermia inducing activity only at dose levels greater than 40 mg./kg. (p.o.) and 15 mg./kg. (i.p.). At the maximum dose-levels of 80 mg./kg. p.o. and 60 mg./kg. i.p. (the highest tested dose-levels which did not induce convulsions), AF102B induced a decrease in the rectal temperature which was similar in its amplitude to those induced by chlorpromazine and oxotremorine. Slight diarrhea was the single cholinomimetic manifestation induced by AF102B at these maximum dose-levels, while oxotremorine induced a full cholinomimetic syndrome associated with tonic-clonic convulsions with this reference material was administered i.p.

Mutagenic activity of AF102B

AF102B was examined for mutagenic activity in five histidine-dependent auxotrophs of *Salmonella typhimurium*, strains TA-15365, TA-100, TA1538, TA-98 and TA-1537, using pour-plate assays. The procedures used complied with the OECD guidelines 471, adopted May 1983. The studies, which were conducted in the absence and presence of an activating system derived from rat liver (S-9 mix), employed a range of levels selected following a preliminary toxicity test in strain TA-98. Each test was conducted in duplicate and was carried out on two separate occasions. Positive controls such as the known mutagens sodium azide, 4-nitro-o-phenylenediamine (NPD), ICR-191 and 2-aminoanthracene, were used under the same experimental conditions. No increases in reversion to prototrophy were obtained with any of the five bacterial strains at the compound levels tested, either in the presence or absence of S-9 mix. No inhibition of growth observed as thinning or absence of the background lawn of non-revertant cells occurred in any strains following exposure to the test material at 1000 ug. per plate. It is concluded that AF102B is devoid of mutagenic activity under the conditions of this study.

Binding affinities of putative cholinergic agonists to muscarinic receptors (A) Scatchard plot:

PNZ is considered as a specific $M_1$ antagonist [See volume dedicated to this topic in Trends Pharmacol. Sci. (Suppl) January 1984]. Its affinity to the receptor is not as high as that of QNB, therefore the apparent Kd should be higher than that of QNB. Indeed the Kd of PNZ, determined by us, was 13.0 nM compared with 0.048 nM found for QNB. The Kd value found by us for PNZ is consistent with the published data.

(B) Displacement of bound [$^3$H]-PNZ by the tested compound:

The advantage of using PNZ lies in its selectivity toward $M_1$-receptor. It should be expected that compounds which are more selective toward $M_1$ receptors will displace it more efficiently. The displacement of [$^3$H]-PNZ by the muscarinic antagonist, atropine and the muscarinic agonist, oxotremorine results in IC$_{50}$'s of $5 \times 10^{-10}$M and $8 \times 10^{-7}$M, respectively and they are both higher than the concentrations needed to displace [$^3$H]-QNB. These results are not surprising in the light of the higher Kd of pirenzepine. The ratio of these two IC$_{50}$'s to the IC$_{50}$'s of the same compound for the displacement of [$^3$H]-QNB can be used as reference for preferential binding of other tested compounds of pirezepine binding sites $M_1$ receptors).

The following table shows the IC$_{50}$'s of the tested compounds for the displacement of [$^3$H]-PNZ or [$^3$H]-QNB. It can be seen that the tested compounds displaced [$^3$H]-PNZ more efficiently than [$^3$H]-QNB. However, AF102B was more selective for $M_1$ receptors by one order of magnitude than the rest of the tested compounds, as expressed by the ratio IC$_{50}^1$:IC$_{50}^2$.

TABLE 1

The potency of putative cholinergic compounds in displacing [$^3$H]—PNZ from central muscarinic receptors (expressed as IC$_{50}$)

| Compound | IC$_{50}^1$[M] | IC$_{50}^2$[M] | IC$_{50}^1$:IC$_{50}^2$ |
|---|---|---|---|
| oxotremorine | $8 \times 10^{-7}$ | $3 \times 10^{-6}$ | 0.27 |
| AF102B | $4 \times 10^{-7}$ | $10^{-5}$* | 0.04 |
| AF102A | $3 \times 10^{-5}$ | $7 \times 10^{-5}$ | 0.43 |

*approximately twice as potent as AF 30 (cis)
IC$_{50}^1$ = IC$_{50}$ for displacement of [$^3$H]—PNZ
IC$_{50}^2$ = IC$_{50}$ for displacement of [$^3$H]—QNB
[Muscarinic receptor assay was performed according to Yamamura and Snyder, PNAS US 71: 1725, (1974).]

TABLE 2

| Guinea-pig ileum induced contractions | | | |
|---|---|---|---|
| COMPOUND | Type of activity | EC$_{50}$ {M} | IC$_{50}$ {M}* |
| Acetylcholine | agonist | $5.0 \times 10^{-8}$ | |
| AF30 | agonist | $4.0 \times 10^{-6}$ | |
| AF102B | agonist | $4.0 \times 10^{-6}$ | |
| AF102A | agonist | >10 | |
| (Ib) | antagonist | | $2 \times 10^{-8}$ |
| (Ic) | antagonist | | $2 \times 10^{-6}$ |

*This dose is the IC$_{50}$ for inhibiting acetylcholine-induced contractions of the ileum.

From TABLES 1 and 2 it is evident that AF102B is a potent muscarinic agonist, whereas its geometrical isomer AF102A is almost one order of magnitude less active; moreover, from TABLE 1 it is evident that AF102B is a selective $M_1$ agonist.

BEHAVIORAL STUDIES

Summary of Results

Behavioral studies in rats treated icv with AF64A (3 nmole/2 ul/side) revealed marked cognitive dysfunctions in a step-through passive avoidance test. These memory impairments could be reversed by physostigmine and by AF102B.

This reversal, as noted in the following table, occurs at low doses at physostigmine (0.06 mg./kg., ip) and AF102B (0.1 and 1 mg./kg., ip and 1 mg./kg., po). Therefore the "therapeutic index" of AF102B is 78–780. This "therapeutic index" is definitely wider than is found in physostigmine (5–17).

Reversal of AF64A-Induced Cognitive Impairments by Physostigmine and AF102B and Their Relative Toxicity in Rats

|  | Physostigmine (mg./kg.) | AF102B (mg./kg.) | |
|---|---|---|---|
|  | ip | ip | po |
| AF64A (3 nmole/side) |  |  |  |
| Passive Avoidance | 0.06 | 1 | 1 |
| Morris Swimming Maze | 0.1 worsens | 1 |  |
| 8-Arm Radial Arm Maze | 0.1 (NS) | 5 |  |
| LD$_{50}$ | 1–2 | 78 | >156 |
| Therapeutic Index | 10–17 | 78–780 15* | >156 |

(NS = non-significant)
*This number is derived by dividing the LD50 by the dose used in the Radial Arm Maze (ip administration).

Moreover, it is important to note that the slope of the acute toxicity curve of AF102B is steep and no overt behavioral signs including parasympathomimetic effects, such as salivation and tremors, were detected up to the lethal dose. Thus, the range of the "sign free" dose is rather wide, emphasizing the potential use of this drug for treatment of SDAT.

Figure 10:
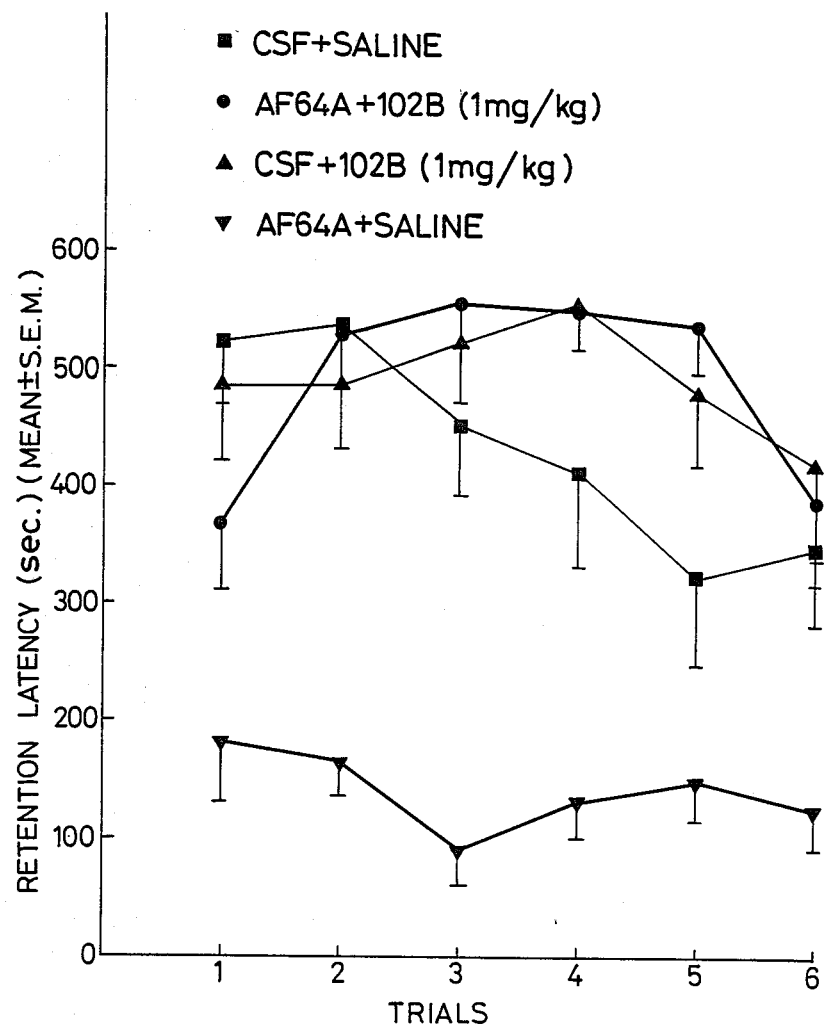
FIG. 10 shows retention-test latency measurements for (inter alia) AF102B in extinction trials.
Figure 11:
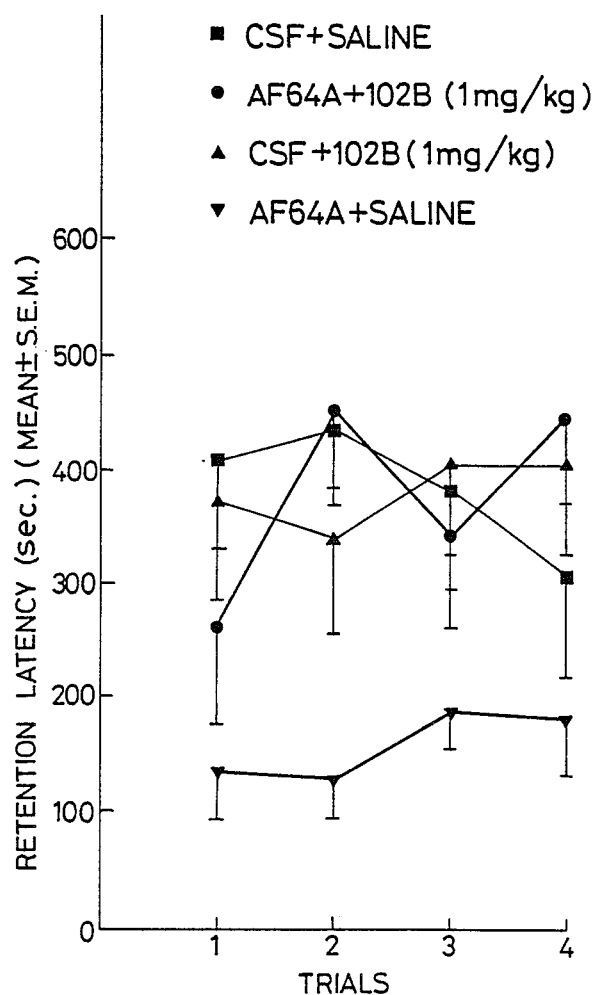
FIG. 11 shows retention-test latency measurements for (inter alia) AF102B in "extinction+latent extinction" trials.

In addition, in the extinction studies performed in the AF64A-treated rats, a very long beneficial effect of AF102B was found, indicating that this compound has long-term duration effects on cognitive functions (FIGS. 10 and 11).

Figure 17:
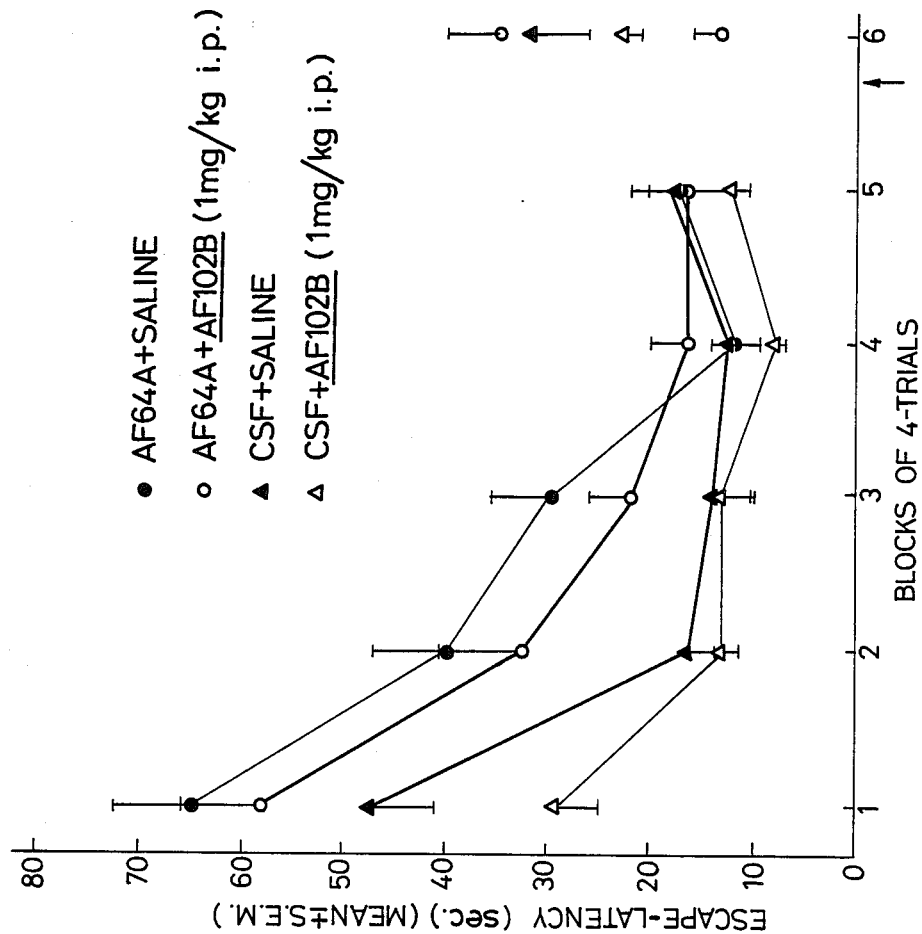
FIG. 17 shows escape latency measures, in blocks of two trials, of AF64A- and CSF-injected groups, after AF102B (1 mg./kg., ip) administration.
Figure 18:
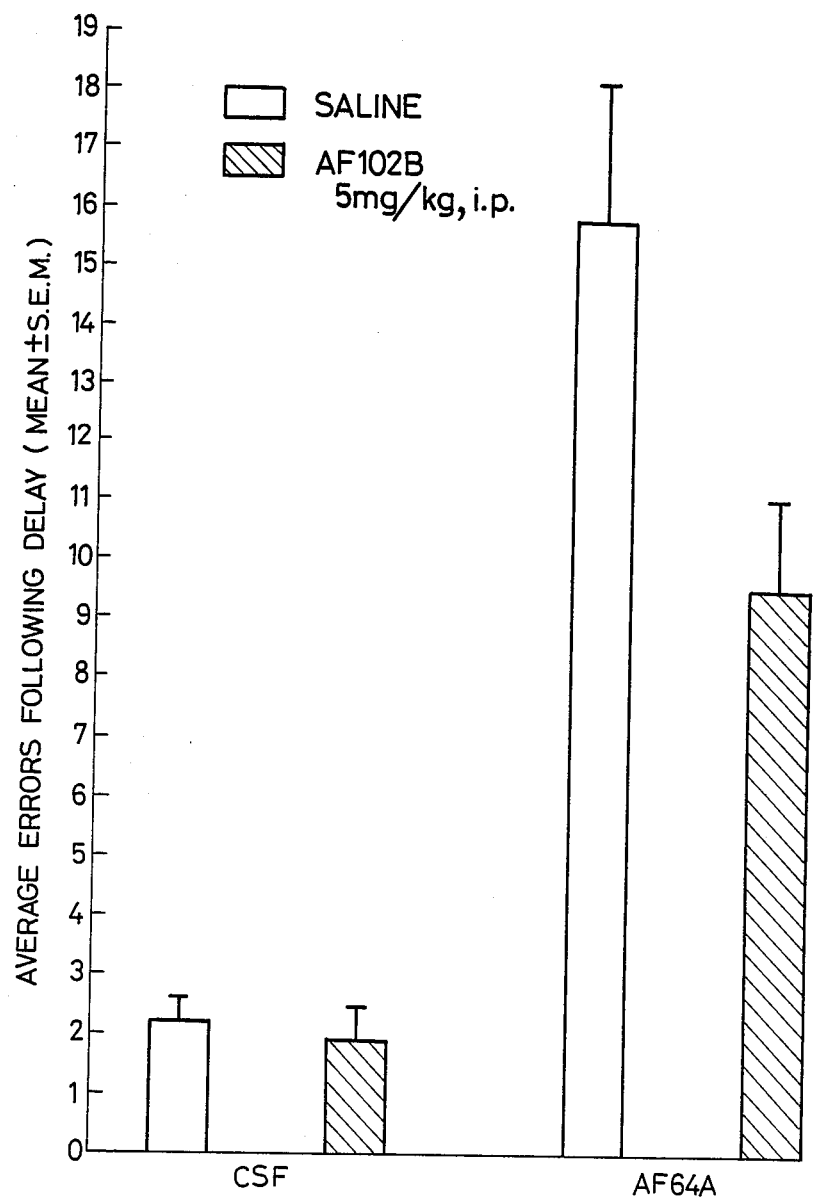
FIG. 18 shows average error in the 8-Arm Radial Maze (RAM) of AF64A- and CSF-injected rats, after AF102B (5 mg./kg., ip) administration.
Figure 19:
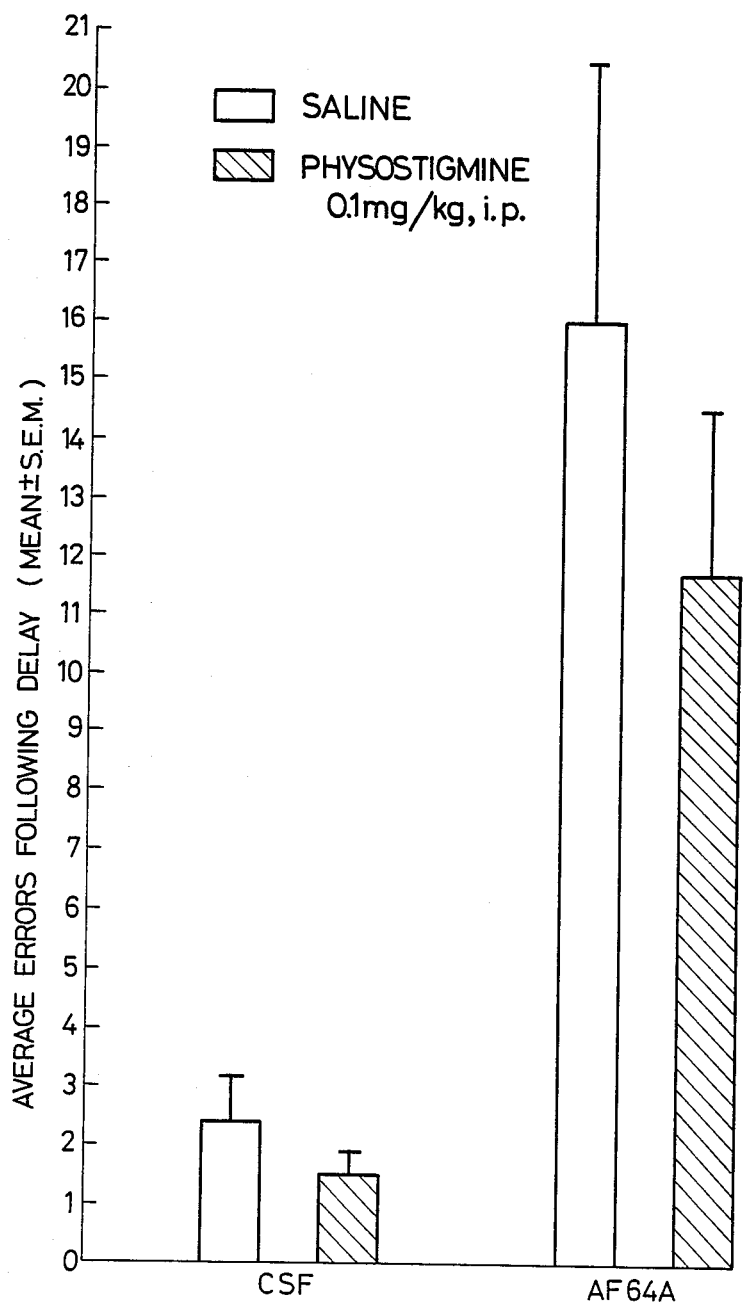
FIG. 19 shows average error in the RAM of AF64A- and CSF-injected rats, after saline and physostigmine administration.

It is also of great importance to note that AF64A (3 nmole/2 ul/side) induced marked memory impairments in the Morris Swimming Maze test (Morris, loc. cit.), which AF102B (1 mg./kg., ip) counteracted, whereas physostigmine (0.1 mg./kg., ip) had a negative effect (FIGS. 16 and 17), Interestingly, the beneficial effects of AF102B in this test were on spatial memory dysfunctions induced by AF64A. In this regard, it is noteworthy that a main memory dysfunction in SDAT patients is impairment of spatial memory. Moreover, it is also of great importance to note that AF64A (3 nmole/2 ul/side) induced memory impairments in the 8-Arm Radial Arm Maze (RAM) which AF102B (5 mg./kg., ip) counteracted, whereas physostigmine (0.1 mg./kg.) had no significant effect (FIGS. 18 and 19).

Experimental

Bilateral icv injections of AF64A produced cognitive impairments in rats in (a) a passive avoidance-step through test; (b) the Morris Swimming Maze; and (c) the Radial Arm Maze; and the possibility of reversal of the AF64A-produced effects by physostigmine as a reference compound, and by AF102B.

AF64A Preparation

AF64A was freshly prepared each day in 10 mM concentration and then diluted in artificial cerebrospinal fluid (CSF) to the proper concentration for injection. The composition of the artificial CSF pH 7.1–7.3 solution was:

|  | mM |
|---|---|
| NaCl | 147 |
| KCl | 2.9 |
| MgCl$_2$.6H$_2$O | 1.6 |
| Dextrose | 2.2 |
| CaCl$_2$.2H$_2$O | 1.7 |

Step-through Passive Avoidance: Experiment 1

The effect of physostigmine on the performance and 24 hours retention of an inhibitory learning (passive avoidance-step through) task, in AF64A and CSF injected rats was investigated, using a post-training drug treatment paradigm.

Male Sprague-Dawley (raised by Charles River) rats, 90–110 days old, weighing 230–360 g., were all allowed free access to food and water. Prior to surgical procedure, rats were anesthetized with Equithesin (0.3 ml./100 g. ip). Bilateral injections were made by stereotaxic application of AF64A or vehicle into the lateral cerebroventricles (icv) (AP—0.8 mm. from bregma, L-1.5 mm. from bregma and —4.7 mm. from skull surface). 23 rats were infused with 3 mole of AF64A in a volume of 2 ul*, into each lateral ventricle (group 1), and 20 control rats were infused similarly with the same volume of CSF (group 2). Altogether 43 rats were operated. The infusion was made by a 28-ga. injection cannula. The rate of injection was kept constant at 0.25 ul/min. The injection cannula was left in place for 4 mins. after injection to allow diffusion of the solutions into the ventricles.
*This dose was found effective in impairing the passive advoidance step-through performance of rats.

27–28 days after injection**, each group of rats were post-operatively subdivided randomly into 2 groups of 10 rats each; subgroup 1 was assigned to the physostigmine treatment and subgroup 2 was treated with saline. Each rat was individually placed in a small lighted front compartment of a two-compartment box. After a 60 sec. familiarization/adaptation period, the door separating the two compartments was opened and a clock activated. The rat's latency to enter the large dark compartment of the box (to step through) was measured. Immediately following entry into the dark compartment, the rat was subjected to an inescapable scrambled foot shock applied to the grid floor (0.6 mA—for 3 secs.). 60 secs after the termination of the shock, at the end of the training procedure, the rat was removed from the dark compartment and physostigmine dissolved in saline (0.06 mg./kg.) or saline placebo were administered ip. Rats were then returned to their home cage. Retention of the passive avoidance task was measured 24 hrs. after training by again placing the rat in the lighted front compartment and after a 60 sec. adaptation period, measuring the latency to enter the dark compartment. The test session ended when a rat entered the dark compartment, or after 600 secs. had elapsed. Animals that failed to step through within 600 secs. were removed from the apparatus and a 600 secs. latency was recorded for them.

**The 27-day interval was found to be effective in impairing the passive avoidance step-through performance in 3 nmole/2 ul AF64A-injected rats.

Results: Mortality and Body Weight

Immediately following surgery the AF64A-injected animals appeared unresponsive to environmental stimuli. A few of the animals (2 out of 20 in the AF64A-injected group and 6 out of 20 in the CSF-injected group) showed a loss of body weight (2%) and 12.5%, respectively), which was observed 7 days following dosing. Within 48 hours of dosing there was a cumulative mortality of 13% of the AF64A-injected group.

Results: Passive Avoidance Test.

The initial latency measures and the retention-test latency measures were analyzed by a two-way ANOVA, Injection (AF64A/CSF) vs. Treatment (physostigmine/saline). Table (i) presents the mean ±S.E.M. of the initial latency measures, while Table (ii) presents the mean ±S.E.M. of the retention-test latency measures.

TABLE (i)

| | Initial-test latency measures (secs.) | |
|---|---|---|
| Injection | AF64A | CSF |
| Pre-Treatment | 3 nmole/2 ul | 2 ul |
| Physostigmine (0.06 mg./kg.) | 25.50 +/− 5.68 | 29.70 +/− 7.93 |
| Saline | 33.80 +/− 9.66 | 16.10 +/− 3.73 |

TABLE (ii)

| | Retention-test latency measures (secs.) | |
|---|---|---|
| Injection | AF64A | CSF |
| Treatment | 3 nmole/2 ul | 2 ul |
| Physostigmine (0.06 mg./kg.) | 458.90 +/− 63.33 | 576.10 +/− 22.69 |
| Saline | 247.90 +/− 52.26 | 556.60 +/− 28.44 |

Figure 8:
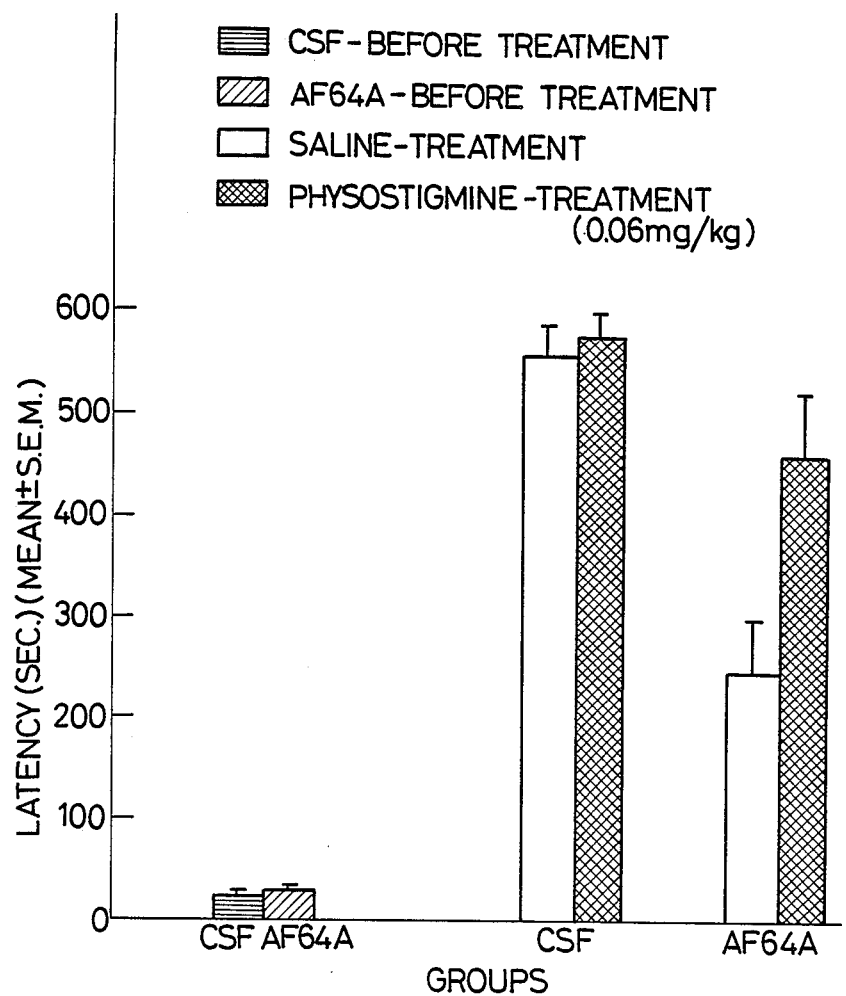
FIG. 8 shows initial and retention-test latency measures of AF64A and CSF-injected groups, before and after physostigmine or saline.

No significant differences were found during the training trial between any of the groups tested (see FIG. 8): $F(1,36) = 0.81$, $p > 0.05$.

The step-through latency of the AF64A-injected group was significantly shorter, $F(1,36) = 20.18$, $p < 0.01$ during the 24 hr. retention test than the CSF-injected group's latency. In addition, the step-through latency of the physostigmine-treated group was significantly longer, $F(1,36) = 5.91$, $p = 0.05$, during the 24 hr. retention-test than the saline-treated group's latency. Retention of a step-through passive avoidance response of the AF64A-injected group was significantly improved by physostigmine administration while the retention of the CSF-injected group was not affected by this treatment (see FIG. 8), $F(1,36) = 4.08$, $p = 0.05$. Shiffe's contrasts of the step through latency measures during the retention test revealed a significant difference between the saline-treated AF64A and CSF-injected groups ($p < 0.05$). The three other contrasts were not significant although the latency of the saline-treated AF64A-injected group appears to be shorter than the latency of the physostigmine-treated AF64A-injected group.

Step-through Passive Avoidance: Experiment 2

The effects of AF102B on the performance and 24 hours retention of an inhibitory learning (passive avoidance-step-through) task, in AF64A and CSF injected rats were investigated, using a post-treatment drug paradigm.

The surgery procedure was identical to that of Experiment 1 except that (1) the weight of the operated rats was 250–325 g.; (2) 20 rats were infused with 3 nmole of AF64A in a volume of 2 ul, into each ventricle (group 1), and 20 control rats were infused with a volume of 2 ul of CSF into each lateral ventricle (group 2). Altogether 40 rats were operated.

The behavioral testing procedure comprised 4 phases. Pretest: 28 male Sprague-Dawley naive rats, 90–110 days old, weighing 270–310 g. were randomly divided into 4 groups of 7 rats each; 3 groups were assigned to AF102B dissolved in saline treatments (0.1, 1 or 5 mg./kg.) and the fourth group was treated with saline. The training and test-retention procedure was identical to that in Experiment 1 except that at the end of the training procedure different doses of AF102B or saline placebo were administered ip.

Phase 1: 27–28 days after injection each group of rats was postoperatively subdivided randomly into 2 groups of 10 rats each; subgroup 1 was assigned to the AF102B treatment and subgroup 2 was treated with saline. The training and the test-retention procedure was identical to that of Experiment 1 except that at the end of the training procedure, the rat was removed from the dark compartment and doses of AF102B dissolved in saline (1 mg./kg.) or saline were administered ip.

Phase 2: 6 days after the retention test, rats were subjected to 6 daily sessions of extinction procedure. The rat was placed in the lighted front compartment and the latency to enter the dark compartment was measured. This procedure was identical to the retention test's procedure in Phase 1.

Phase 3: After the extinction procedure, rats were subjected to a latent extinction procedure. The rat was placed in the lighted front compartment and after a 60 sec. adaptation period, was pushed into the dark compartment and kept there for 60 secs. This procedure was followed once a day for three days. After the latent-extinction procedure, rats were subjected to an "extinction+latent extinction" procedure. The rat was placed in the lighted front compartment and after a 60 sec. adaptation period, the latency to enter the dark compartment was measured. The test session ended when a rat entered the dark compartment. Animals that failed to step through within 600 secs. were pushed into the dark compartment and a 600 secs. latency was recorded for them. This procedure was followed once a day for 4 days. At the end of the 4th session, immediately following entry into the dark compartment, the rat was subjected to a training and retention-test procedure identical with that in Phase 1 except that the two sub-groups treated in Phase 1 with AF102B were now treated with saline placebo and vice-versa. (It should be noted that this treatment took place 2 months after the AF6-4A/CSF injection).

Results: Mortality and Body Weight.

Immediately following surgery the AF64A-injected animals appeared unresponsive to environmental stimuli. A few of the animals (2 out of 20 in the AF64A-injected group) showed a 2% loss of body weight which was observed 7 days following dosing. Within 48 hours of dosing no mortality occurred in any of the groups.

Results: Passive Avoidance Test.

Pretest.

The initial latency measures and the retention-test latency measures were analyzed by a one-way ANOVA. Table (iii) presents the mean ±S.E.M. of the initial latency measures, while Table (iv) presents the mean ±S.E.M. of the retention-test latency measures.

TABLE (iii)

| Initial latency measures (secs.) | | | |
| --- | --- | --- | --- |
| AF102B 0.1 mg./kg. | AF102B 1 mg./kg. | AF102B 5 mg./kg. | Saline |
| 16.71 +/− 4.77 | 11.86 +/− 1.23 | 19.71 +/− 5.39 | 20.00 +/− 5.46 |

TABLE (iv)

| Retention-test latency measures (secs.) | | | |
| --- | --- | --- | --- |
| AF102B 0.1 mg./kg. | AF102B 1 mg./kg. | AF102B 5 mg./kg. | Saline |
| 330.57 +/− 75.55 | 348.14 +/− 81.66 | 551.71 +/− 32.92 | 513.00 +/− 56.39 |

No significant differences were found during the training trial between any of the groups tested, $F(3,24)=0.57$; $p>0.05$. In addition, no significant differences were found during the 24 hr. retention-test between the different doses of AF102B, $F(3,24)=2.61$; $p<0.05$, although the retention latency of the 0.1 mg./kg. and the 1 mg./kg/ groups tends to be shorter than the latency of the 5 mg./kg. and the saline groups.

Phase 1.

The initial latency measures and the retention-test latency measures were analyzed by a two-way ANOVA, Injection (AF64A/CSF) vs. Treatment (AF102B/Saline). Table (v) presents the mean ±S.E.M. of the initial latency measures, while Table (vi) presents the mean ±S.E.M. of the retention-test latency measures.

TABLE (v)

| | Initial-test latency measures (secs.) | |
| --- | --- | --- |
| Injection Treatment | AF64A 3 nmole/2 ul | CSF 2 ul |
| AF102B (1 mg./kg.) | 18.40 +/− 3.74 | 15.30 +/− 2.83 |
| Saline | 22.66 +/− 4.43 | 15.20 +/− 2.10 |

TABLE (vi)

| | Retention-test latency measures (secs.) | |
| --- | --- | --- |
| Injection Treatment | AF64A 3 nmole/2 ul | CSF 2 ul |
| AF102B (1 mg./kg.) | 514.10 +/− 38.21 | 447.60 +/− 58.09 |
| Saline | 182.44 +/− 29.90 | 574.30 +/− 16.39 |

Figure 9:
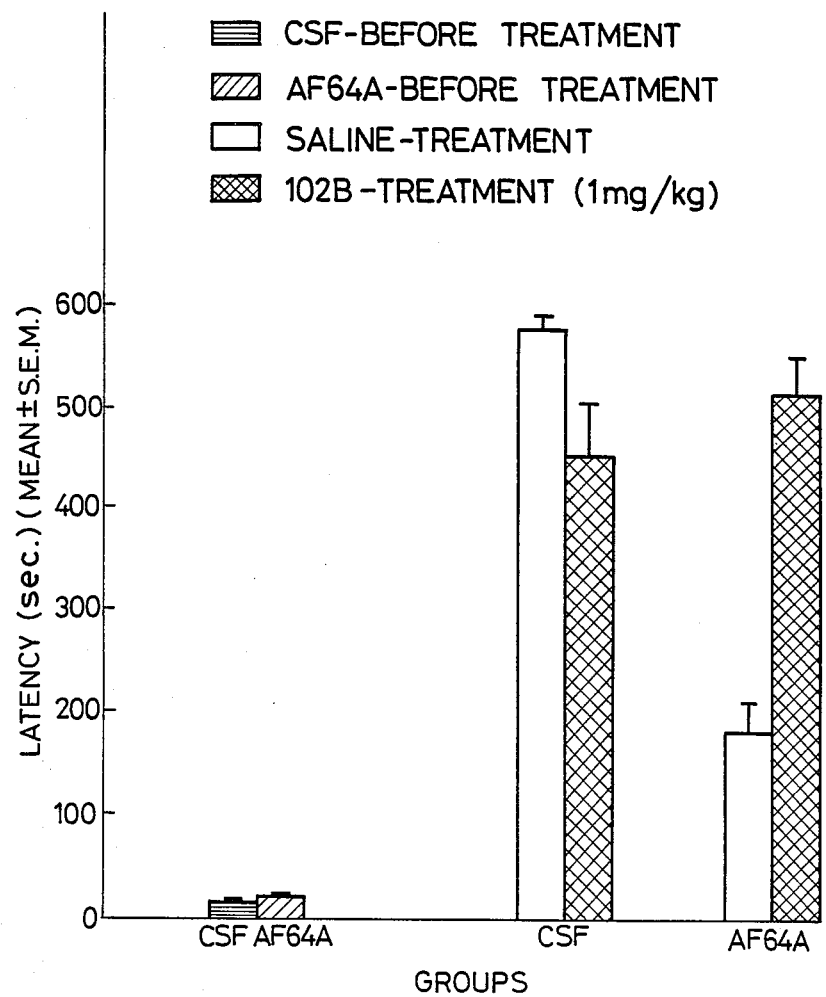
FIG. 9 shows initial and retention-test latency measures of AF64A- and CSF-injected groups, before and after AF102B or saline.

No significant differences were found, during the training trial, between any of the groups tested (see FIG. 9).: $F(1,35)=2.16$, $p>0.05$ for the injection variable (AF64A/CSF) main effect. For the other main effect (the two groups to be treated with AF102B or saline): $F(1,35)=0.29$; $p>0.05$.

The step-through latency of the AF64A-injected group was significantly shorter, $F(1,35)=13.89$; $p<0.01$, during the 24 hr. retention test than the CSF-injected group's latency. In addition, the step-through latency of the AF102B-treated group was significantly longer, $F(1,35)=4.98$; $p<0.05$, during the 24 hr. retention test than the saline-treated group's latency.

Retention of a step-through passive avoidance response of the AF64A-injected group was significantly improved by AF102B administration, while that of the CSF-injected group was significantly impaired (see FIG. 9), $F(1,35)=31.18$, $p<0.01$. Shiffe's contrasts of the step through latency measures during the retention test revealed that all the between-groups differences were significant ($0.01<p<0.05$) except the AF6-4A+AF102B vs. CSF+AF102B difference.

Phase 2.

The retention-test latency measures during the extinction period was analyzed by a three-way ANOVA (6×2×2) with one repeated variable (Trials) and two non-repeated variables (Injection—AF64A/CSF and Treatment—AF102B/CSF). FIG. 10 shows that the step-through latency of the AF64A-injected group was significantly shorter, $F(1,36)=16.83$; $p<0.01$, than the CSF-injected group's latency. In addition, the step-through latency of the AF102B-treated group was significantly longer, $F(1,36)=31.45$, $p<0.01$, than the saline-treated group's latency. Retention of a step through-passive avoidance response of both the AF64A and the CSF-injected groups, during extinction, was significantly improved by AF102B administration. $F(1,36)=15.80$, $p<0.01$. Shiffe's contrasts of the step-through latency measures during the extinction period revealed that all the between-groups differences were significant ($p<0.01$) except the AF64A+AF102B vs. CSF+AF102B difference.

The trials variable main effect during extinction was significant, $F(5,180)=2.68$, $p<0.05$. Contrasts analysis showed that the retention latency of the second extinction trial was significantly longer than the latency of the 6th trial ($p<0.05$). there were no other significant differences.

The interaction between treatment and trials was significant, $F(5,180)=3.30$, $p<0.05$. Significant simple main effects contrasts were found between the AF102B-treated groups and the saline-treated groups during all the extinction trials except the first trial. In addition, the retention latency extinction curve was significantly different from that of the saline-treated groups ($p<0.05$). The retention latency of the AF102B-treated groups increased from the first to the fourth trial and then decreased. The retention latency of the saline-treated groups decreased from the first trial to the sixth trial.

Phase 3.

A. The retention-test latency measures during the "extinction+latent extinction" period was analyzed by a three-way ANOVA (4×2×2) with one repeated variable (Trials) and two non-repeated variables (Injection—AF64A/CSF and Treatment AF102B/CSF). No significant differences were found during "extinction+-latent extinction" period between any of the conditions tested, in the retention-test latency measures, although the retention latency of the saline-treated AF64A-injected group appears to be shorter than the retention latency of the three other groups (see FIG. 11).

B. The retention-test latency measures of the second administration of AF102B/Saline were analyzed by a two-way ANOVA, Injection (AF64A/CSF) vs. Treatment (AF102B/Saline). Table (vii) presents the mean ±S.E.M. of the retention-test latency measures.

TABLE (vii)

Retention-test latency measures (secs.) of second administration of AF102B/Saline

| Injection Treatment | AF64A 3 nmole/2 ul | CSF 2 ul |
|---|---|---|
| AF102B (1 mg./kg.) (previously Saline) | 580.40 +/− 18.61 | 600 |
| Saline (previously AF102B) | 600 | 600 |

Figure 12:
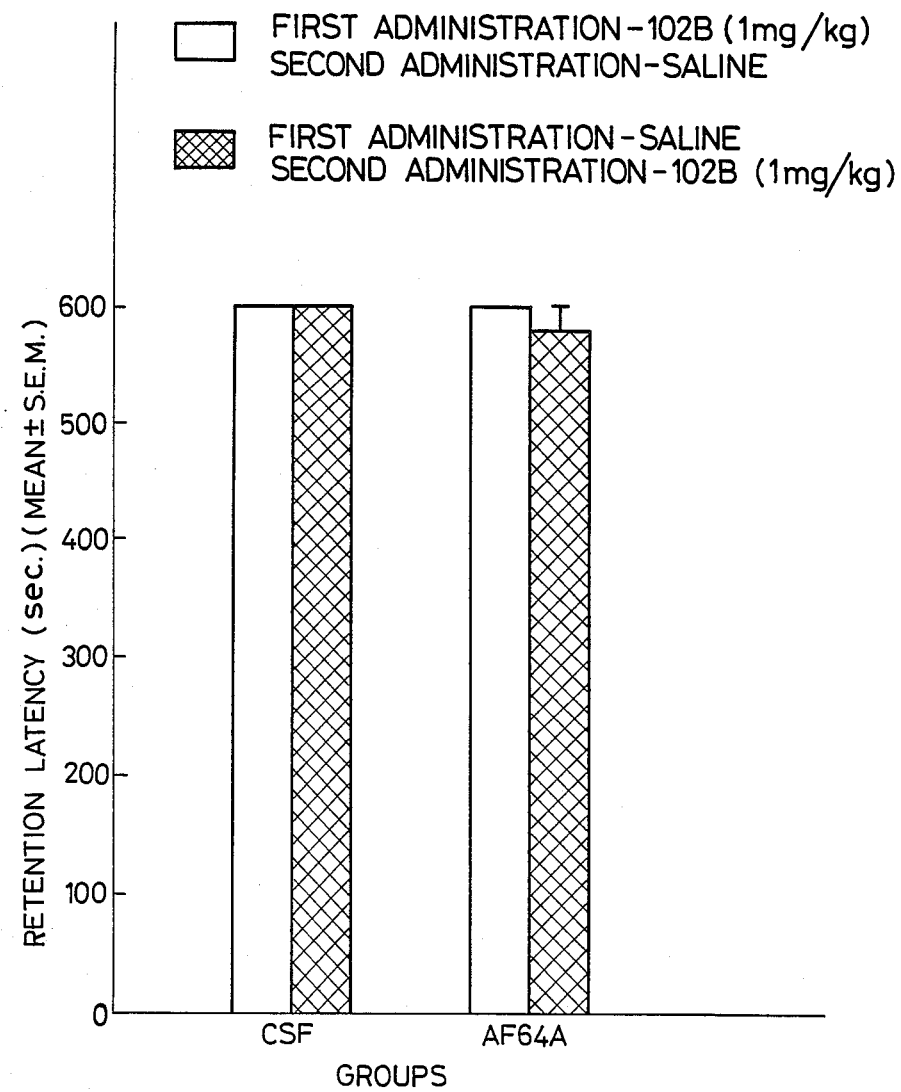
FIG. 12 shows retention-test latency measures of AF64A- and CSF-injected groups, after second administration of AF102B or saline.

No significant differences were found following the second AF102B/Saline administration between any of the groups tested (p>0.05) (see FIG. 12). The retention latency of the Saline-treated AF64-A injected group, previously treated with AF102B, remained in the same level, while the retention latency of the AF102B-treated AF64A-injected group, previosly treated with saline, increased and reached the level of the CSF-injected groups.

BEHAVORIAL EXPERIMENTS

The present work investigated further the possibility of reversal of the AF64A-induced effects by various doses of AF102B in the passive avoidance task and in two other tasks, namely, the Morris Swimming Maze and the 8-Arm Radial Maze.

Passive Avoidance Task

Experiment 1

In this experiment we investigated the effect of AF102B (0.1 mg./kg., ip) administration on the performance and 24 hours retention of an inhibitory learning (passive avoidance-step through) task in AF64A and CSF-injected rats, using a post-training drug treatment paradigm.

Surgery

Male Sprague-Dawley (raised by Charles River) rats, 90–110 days old, weighing 265–340 g. were injected icv. 10 rats were infused with 3 nmole of AF64A in a volume of 2 ul, into each lateral ventricle (group 1), and 10 control rats were infused with CSF (group 2). Altogether 20 rats were operated.

Behavorial Testing

The behavioral testing procedure comprised two phases, 1 and 2. In a pretest training procedure each rat was individually placed in a small lighted front compartment of a two-compartment box. After a 60 secs. familiarization/adaptation period, the door separating the two compartments was opened and a clock activated. The rat's latency to enter the large dark compartment of the box (to step-through) was measured. Immediately following entry into the dark compartment, the rat was subjected to an inescapable scrambled foot shock applied to the grid floor (0.6 mA for 2 secs.). Sixty secs. after the termination of the shock, at the end of the training procedure, the rat was removed from the dark compartment and saline placebo was administered i.p. Rats were then returned to their home cage. Retention of the passive avoidance task was measured 24 hr. after training by again placing the rat in the lighted front compartment, and after a 60 secs. adaptation period, measuring the latency to enter the dark compartment. The test session ended when a rat entered the dark compartment or after 600 secs. had elapsed. Animals that failed to step through within 600 secs. were removed from the apparatus and a 600 secs. latency was recorded for them.

Phase 1

27–29 Days after AF64A or CSF injection, each group of rats was subjected to the same training and the test-retention procedure as in the pretest except that: (a) in the training procedure, the rat was treated i.p. with saline placebo; (b) the duration of the shock was 3 secs.

Phase 2

13–20 Days after the retention test (40–47 days after AF64A of CSF injection) the rats were subjected to a second passive avoidance test. Each rat was placed in the lighted front compartment and after a 60 secs. adaptation period, the latency to measure the dark compartment was measured. Animals that failed to step through within 600 secs. were pushed into the dark compartment and a 600 secs. latency was recorded for them. Rats were subjected to training and retention-test procedures identical to the procedures in phase 1 except that groups treated with saline were now treated with AF102B (0.1 mg.kg., ip.).

Results

Mortality and Body Weight

Immediately following surgery the AF64A-injected animals appeared unresponsive to environmental stimuli. One animal (out of 20 AF64A-injected animals), showed a 2% loss of body weight, and two animals did not show an increase in body weight 7 days following injection. No mortality occured in any of the groups.

Passive Avoidance Test: Pretest

No significant differences were found during the training trial between any of the groups tested [F(3,24)=0.22; p>0.05].

AF102B (0.1 mg./kg., i.p.)

Comparison was made between the retention-test latencies obtained after administration of AF102B (0.1 mg./kg., i.p.) (second running) and the retention-test latencies obtained after saline-administration (first running). The retention-test latency measures were analyzed by a 2-way ANOVA (2×2) with one repeated variable (Treatment+Running) and one non-repeated variable [Injection (AF64A/CSF)].

Figure 13:
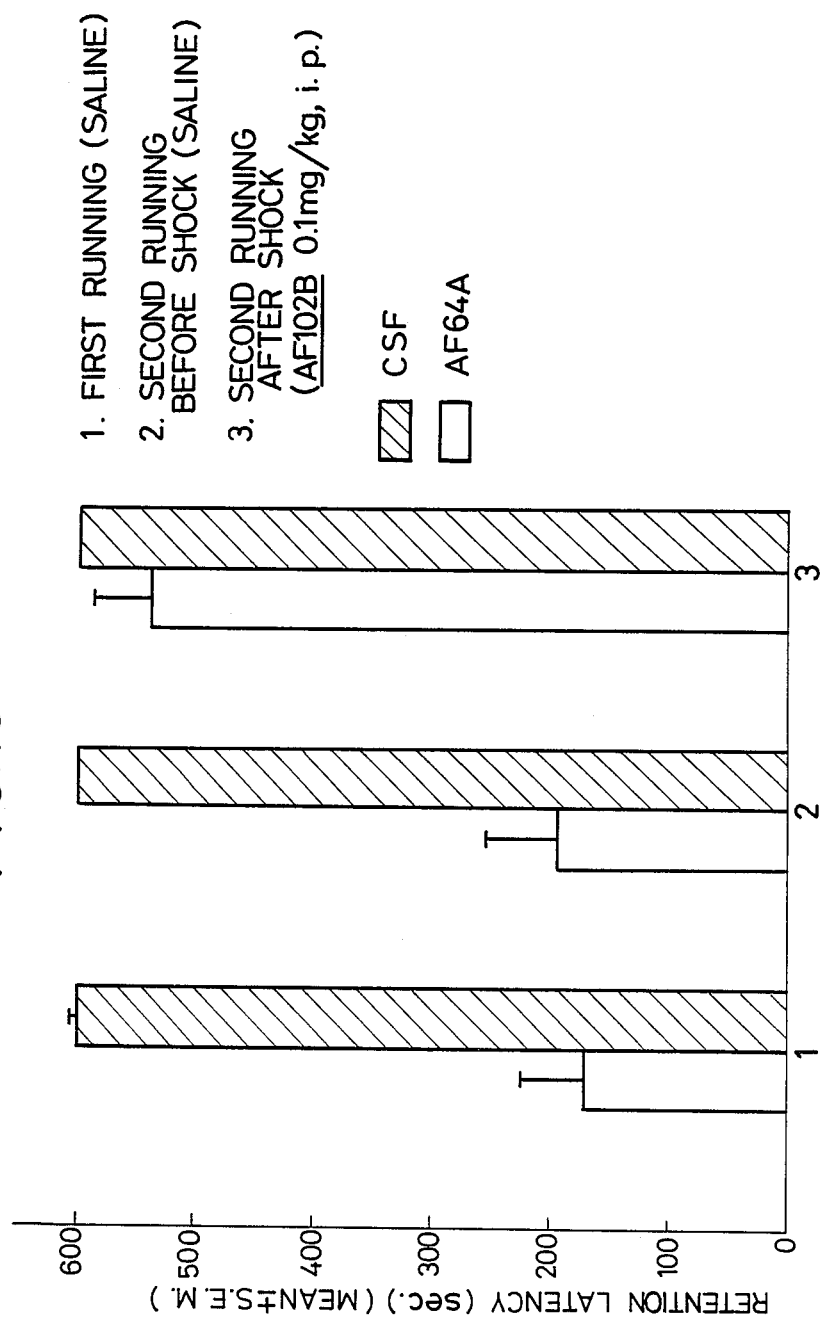
FIG. 13 shows retention-test latency measures of AF64A- and CSF-injected groups, after AF102B (0.1 mg./kg., ip) or saline administration.

The retention latency of the AF64A-injected group was still significantly shorter [F(1,18)=29.48; p<0.001] than the CSF-injected group's latency (see FIG. 13). In addition, the retention latency of the AF102B-treated groups (second running) was significantly longer [F(1,18)=33.71; p<0.001) than the saline-treated group's latency (first running). Retention of a step through-Passive Avoidance response of the AF64A-injected group was significantly improved by AF102B administration [A(1,18)=33.27; p<0.001) while that of the CSF-injected group did not significantly change by this treatment. Indeed, since latencies of CSF treated rats were already close to 600 secs., no change was really expected. Shiffee's contrasts revealed that AF64A+AF102B vs. AF64A+saline difference and AF64A+saline vs. CSF+saline difference were significant (p<0.001). It is pointed out, however, that the improvement of the AF64A-injected group by AF102B administration was recorded, in this case, after a second shock, a fact which might have influenced the improvement in retention.

Experiment 2

This experiment investigated the effect of AF102B (p.o.) administration on the performance and 24 hours retention of an inhibitory learning (Passive Avoidance step-through) task, in AF64A- and CSF-injected rats, using post-training treatment paradigm.

Method

Surgery

The surgery procedure was identical to the surgery procedure in Experiment 1, except: (1) the weight of the operated rats was 265-320 g.; (2) 10 rats were infused with 3 nmole of AF64A in a volume of 2 ul, into each lateral ventricle (group 1) and 10 control rats were infused with 2 volumes of 2 ul of CSF into each lateral ventricle (group 2). Altogether 20 rats were operated.

Behavioral Testing

The behavioral testing procedure comprised 2 phases.

Phase 1

The training and test-retention procedures of phase 1 were identical to the procedures of phase 1 in Experiment 1 except that: (1) each group of rats was post-operatively subdivided; and (2) at the end of the training procedure the rat was removed from the dark compartment and AF102B (1 mg./kg., p.o.) or saline were administered.

Phase 2

19-22 Days after the retention test (49 days after AF64A or CSF injection) the saline-treated rats only were subjected to a second running. The training and test-retention procedures were identical to the procedures in phase 2 of Experiment 1 except that the two subgroups treated in phase 1 with saline were now treated with AF102B (1 mg./kg., p.o.).

Results

Phase 1

The initial latency measures of the AF64A- and CSF-injected groups were analyzed by a t-test for independent samples. The following tables present respectively (a) the means ±S.E.M. of the initial latency measures and (b) the means ±S.E.M. of the retention-test latency measures.

| (a) Initial-test latency measures (secs.) | |
|---|---|
| AF64A | CSF |
| 3 nmole/2 ul/side | 2 ul/side |
| 19.0 +/− 2.18 | 18.86 +/− 2.07 |

| (b) Retention-test latency measures (secs.) | | |
|---|---|---|
| Injection Treatment | AF64A 3 nmole/2 ul/side | CSF 2 ul/side |
| AF102B | 524.55 +/− 45.60 | 600 |
| Saline | 168.90 +/− 28.91 | 548.90 +/− 48.51 |

Figure 14:
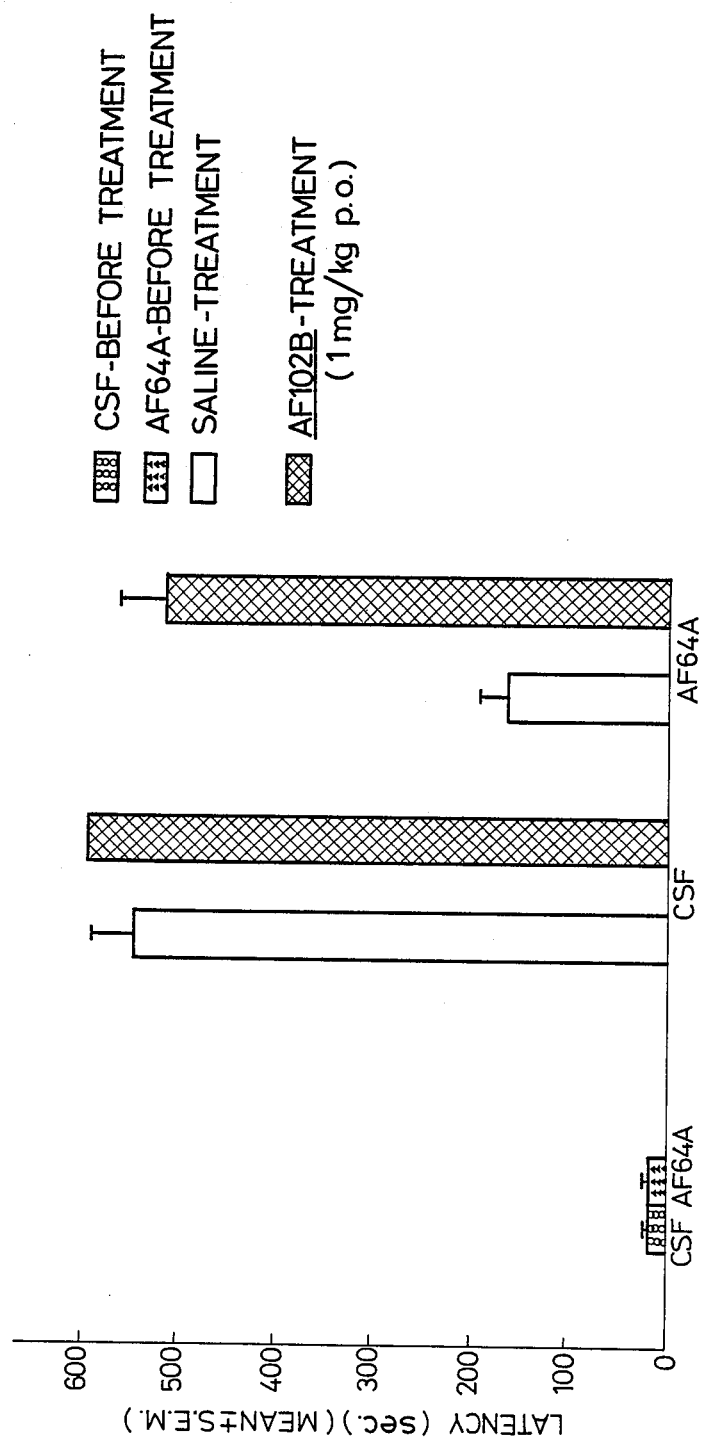
FIG. 14 shows latency measures (sec.) of AF64A- and CSF-injected groups, before and after AF102B (1 mg./kg., po) or saline administration.

No significant differences were found during the training trial, between the AF64A- and CSF-injected groups (see FIG. 14), $t(57)=0.05$; $p>0.05$. The first analysis of the retention latency measures showed that the step-through latency of the AF64A-injected group was significantly shorter $[F(1,36)=37.01; p<0.001]$ (see FIG. 14) during the 24 hr. retention test than the CSF-injected group's latency.

The second analysis of the retention latency measures showed that the step-through latency of the AF64A-injected group was significantly shorter $[F(1,35)=37.93; p<0.001]$ (see FIG. 14) during the 24 hr. retention test than the CSF-injected group's latency. In addition, the step-through latency of the AF102B-treated group was significantly longer $[F(1,35)=28.46; p<0.001]$ than the saline treated group's latency. Retention of a step-through passive avoidance response of the AF64A-injected group was significantly improved by AF102B administration $[F(1,35)=13.94; p<0.001]$ while there was no significant difference between the AF102B-treated-CSF-injected group and the saline-treated-CSF-injected group. Shiffee contrasts revealed that the AF64A+AF102B vs. AF64A+saline difference was significant ($p<0.001$).

Phase 2

Figure 15:
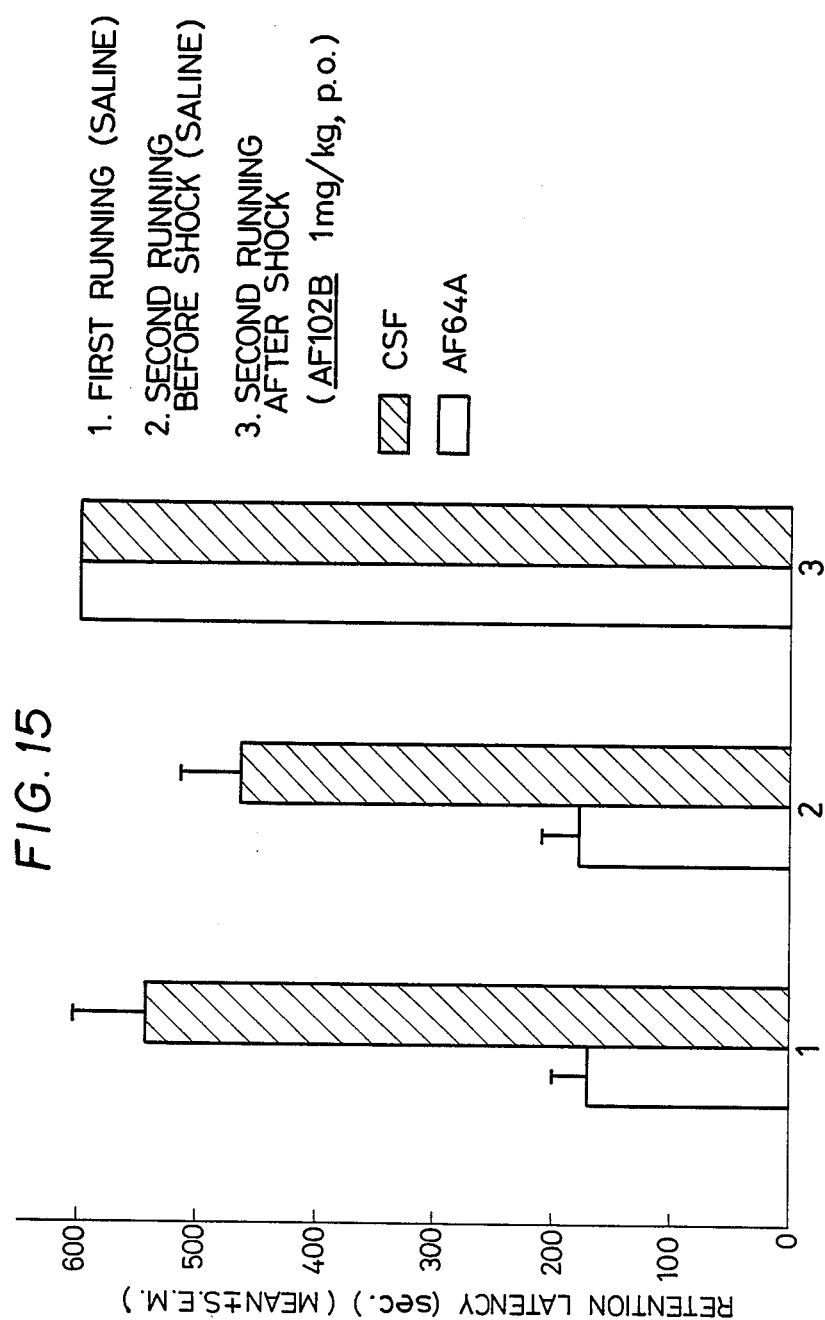
FIG. 15 shows retention test latency measures (sec.) of AF64A- and CSF-injected groups, before and after AF102B (1 mg./kg., po) or saline administration.

In a first analysis, the retention-test latency measures before the shock administration in the second running were compared to the retention-test latency measures during the first running. The retention-test latency measures were analyzed by a 2-way ANOVA ($2\times2$) with one repeated variable (running) and one non-repeated variable [injection (AF64A/CSF)]. The retention latency of the AF64A-injected group was still significantly shorter $[F(1,18)=49.51; p<0.001)$ 19-22 days after the first running, than the CSF-injected group's latency (see FIG. 15). There was neither a significant running effect $[F(1,18)=0.91; p>0.05)$ nor a significant interaction effect $[F(1,18)=1.28; p>0.05)$.

In the second analysis the retention-test latency measures after the shock administration during the second running wer compared to the retention-test latency measures during the first running. The retention-test latency measures were analyzed by a 2-way ANOVA ($2\times2$) with one repeated variable (running + treatment) and one non-repeated variable [injection (AF64A/CSF]. The retention latency of the AF64A-injected group was still significantly shorter $[F(1,18)=40.81, p<0.001)$ than the CSF-injected group's latency (see FIG. 15). In addition, the retention latency of the AF102B treated group (second running) was significantly longer $[F(1,18)=65.71; p<0.001]$ than the latency of the saline-treated group (first running). Retention of a step through-passive avoidance response of the AF64A-injected group was significantly improved by AF102B administration $[F(1,18)=40.81; p<0.001]$ while that of the CSF-injected group did not significantly change by this treatment. Shiffee contracts revealed that the difference of AF64A+AF102B vs. AF64A+saline was significant.

Morris Swimming Maze

Cholinergic deficiency, as well as treatments with anticholinergic drugs, were shown to impair memory and learning processes associated with spatial orientation (Sutherland et al, J. Comp. Physiol. Psychol. 96: 563-73, 1982). In this respect, the water-maze (Morris, Learning and Motivation, 12: 239-61, 1978) seemed to be a suitable behavioral paradigm for the detection of cognitive impairments induced by AF64A in rats, and of their reversal by cholinergic drugs. Since physostigmine is currently one of the few cholinergic drugs used in Alzheimer's patients, it was selected for preliminary testing of its effects on AF64A treated rats.

38 male Sprague Dawley rats (raised by Charles River) 5-6 months old with an average weight of 500 g. were used. The rats were housed in groups of 5 and were given free access to food and water. Testing was carried out in a round white metal tub 1.4 m. diameter and 0.4 m. deep. The tub was filled with water, made opaque by milk powder to the level of 18 cm. A platform of 12 cm. diameter and at a height of 16 cm. was placed in the tub 2 cm. below water level. The platform was covered with gauze to prevent the animal from slipping back into the water after reaching the platform.

Prior to testing, the rat was placed on the platform for 120 secs., placed gently into the water, facing the wall of the pool, at one of four starting locations (north, south, east or west) around the pool's perimeter. Within each block of four trials, each rat was started at each of the four starting locations, with the sequence of starting locations randomly selected. Testing was carried out on 2 consecutive days with each rat submitted daily to eight trials. During trials 1–12 the platform was located in the center of the south-east quadrant and during trials 13–16 the platform was transferred to the center of the north-west quadrant. If in a particular trial the rat found the platform, it was permitted to remain on it for 60 secs. before starting the next trial. If a rat failed to find the platform, the trial was terminated after a cut-off time of 120 secs., and subsequently was put on it for 60 secs. before starting the next trial. The latency to find the platform was measured.

For drug testing, rats were injected with AF64A or CSF (3 nmole/2 ul/side) as described in Experiment 2, above. The rats were subjected first to a step-through learning procedure (see Experiment 1, above) and were 3-3.5 months after injection when tested in the water maze. The rats were divided into 4 groups; 18 CSF-injected rats were treated either with physostigmine (0.1 mg./kg. ip) (10 rats) or with saline (8 rats). 20 AF64A-injected rats were divided similarly. The rats were injected with physostigmine immediately before testing on each day.

Results.

Figure 16:
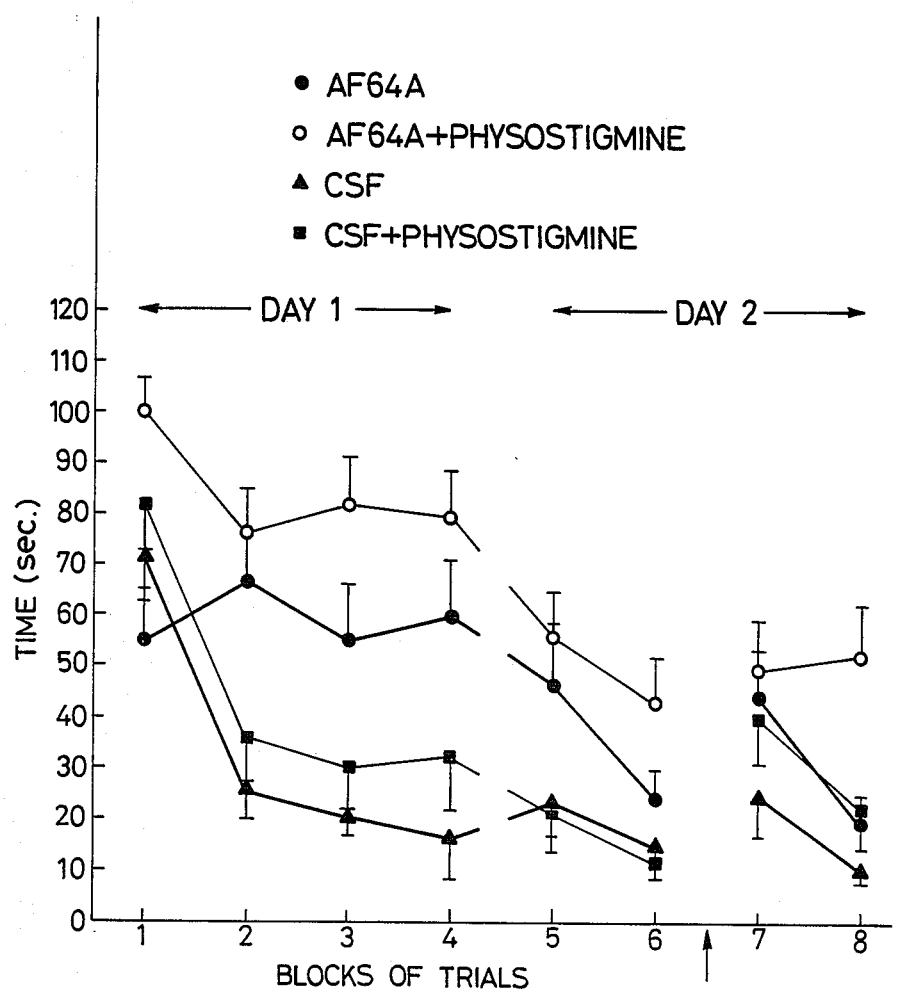
FIG. 16 shows escape latency measures, in blocks of two trials, of AF64A- and CSF-injected groups, after physostigmine administration.

The escape latency was analyzed by a 3-way ANOVA (4×2×2) with one repeated variable (trials) and two non-repeated variables (Injection—AF64A/CSF and Treatment—physostigmine/saline). Table (viii) presents the escape-latency of the groups tested. FIG. 16 depicts that AF64A injected rats showed an increase in escape latency (in seconds) relative to CSF treated rats. This effect is highly significant, $F(1,34)=14.88$, $p<0.001$. The initial escape-latency for all four groups was similar. However, the escape-latency of the CSF-treated rats decreased faster than the escape-latency of the AF64A rats. Physostigmine apparently impaired the performance of both AF64A and CSF-injected groups, compared with non-treated AF64A and CSF-injected groups but this result was not statistically significant. The trials effect was statistically significant, $F(15,510)=5.9$, $p<0.001$. In addition, a significant interaction between trials and physostigmine was found, $F(15,510)=4.3$, $p<0.001$; physostigmine inhibited the decrease of the escape-latency curve, regardless of the injected group.

When similar Morris Swimming Maze experiments were carried out on AF102B (1 mg./kg., ip), it was found that this compound definitely improved the memory deficits induced by AF64A (FIG. 17), whereas physostigmine (0.1 mg./kg., ip) had a negative effect. The beneficial effects of AF102B in this test were on spatial memory dysfunctions induced by AF64A. It is noteworthy that in this respect, a main memory dysfunction in SDAT patients is impairment of spatial memory. Details of these experiments are given in the description which follows.

Morris Water Maze: Method and Results a. Subjects

Forty male Sprague-Dawley rats (obtained from Charles River Breeding Laboratories U.K.), 5–6 months old, weighing 450–580 g. during the experiment served as subjects. Rats were housed in groups of 5 and were given free access to food and water. 2.5–3.5 months before behavioral testing, rats were injected with AF64A (3 nmole/2 ul/side) (20 rats-group 1) or CSF (20 rats-group 2) as described in the surgery procedure.

(b) Drug Administration

Each of the injected groups was randomly subdivided into two equal size treatment groups. At the end of the training procedure, in the first and second day of behavioral testing, one of the AF64A-injected subgroups and one of the CSF-injected subgroups (n=20) were treated with AF102B dissolved in saline (1 mg./kg., i.p.) while the other two subgroups (n=20) were treated with saline.

AF102B (1 mg./kg., i.p.)

The escape latency of this treatment was analysed by a 3-way ANOVA (4×2×2) with one repeated variable (trials) and two non-repeated variables [injection (AF64A/CSF) and treatment (AF102B/saline]. FIG. 17 depicts that AF64A-injected rats showed a significant increase in escape latency relative to CSF-injected rats $[F(1,36)=11,26; p<0.005]$. In addition, AF102B-treated rats showed a significant decrease in escape latency relative to saline treated rats $[F(1,36)=4.89; p<0.05]$ regardless of the groups injected. The trials effect was statistically significant $[F(5,180)=33.34; p<0.001]$; in addition, a significant interaction between trials and injection was found $[F(5,180)=5,53; p<0,001)$; the escape latency of the CSF-injected rats decreased faster than the escape latency of the AF64A-injected rats.

8-Arm Radial Arm Maze

Introduction

In the 8-Arm Radial Arm Maze, AF64A (3 nmole/2 ul/side) induces memory impairments. In this study, the effects of AF102B and physostigmine were evaluated in AF64A- and CSF-treated rats. Experiments were carried out on the effect of AF102B (5 mg./kg., ip), as well as on physostigmine (0.1 mg./kg., ip), in both cases on trained rats with 2 hours delay.

Method

In all experiments Sprague Dawley rats were used (Charles River Breeding Laboratories U.K.); they were housed individually and were deprived of food until reaching 85% of their free feeding weight. The room was illuminated 12 hours per day (6:00 to 18:00) and behavorial training and testing sessions were carried out during the day. After reaching 85% of free feeding weight, rats received 3 food pellets (Labena) per day and had free access to water. Two days before training began, animals were faimilarized with 45 mg. precision pellets (Bioserv Inc) which were later used for reinforcement in the maze.

The same surgery procedure was used as in the passive avoidance and Morris Swimming Maze tests.

Procedure

A group of 20 rats, which were first used in a passive avoidance test, were trained in the new maze 7 weeks post injection. Following 6 days of training a period of 2 hours delay was inserted. Rats were allowed to collect 4 pellets, then they were returned from the maze to their cages. After 4 hours delay they were put back in the maze until they collected the remaining 4 pellets or until 5 minutes had elapsed.

Experiment 1

The same group of rats was injected with AF102B (5 mg./kg., ip) or saline (1 ml./kg., ip), immediately following picking the first 4 baits. The effects on performance were tested 2 hours post injection. Each rat received both treatments twice. A 1 day interval was given between the AF102B treatment and the saline treatment and two days between the sets of treatments.

Experiment 2

A week later, the same group of rats was injected with physostigmine (0.1 mg./kg., ip) or saline (1 ml./kg., ip), immediately following picking the first 4 baits. The effects on performance were tested 2 hours post injection.

Results and Discussion

Experiment 1

The treatment with AF102B (5 mg./kg., ip) immediately following completion of the first four choices had a significant effect on performance (FIG. 18). Analysis of the results in a 2 factors mixed design: repeated measures on one factor showed a significant ($p<0.001$, $F=17.5$) decrease in the mean number of errors for the AF64A injected rats when compared to their controls (AF64A injected rats treated with saline). A significant effect ($p<0.005$, $F=14.5$) was found between trials (treatment with AF102B vs. saline) and conditions (AF64A icv injections vs. CSF icv injections). The AF102B treatment improved performance only when rats were previously injected icv with AF64A.

Experiment 2

Treatment with physostigmine (0.1 mg./kg., ip) had no significant effect on the performance of the rats ($p>0.05$, $F=4.03$) (FIG. 19) although there is a tendency for an apparent improvement following physostigmine. However, the differences between the AF64A injected rats and the CSF injected rats remained significant ($p<0.005$, $F=11.4$).

Conclusions

The Radial Arm Maze procedure has been extremely successful in proving that: (1) there is a significant difference in the performance of AF64A as compared with the CSF-treated rats, and (2) memory impairment could be reversed by AF102B (5 mg./kg., ip).

SUMMARY OF BEHAVIORAL STUDIES

The table which follows summarizes the relevant data regarding AF102B, oxotremorine and pirenzepine, illustrating the outstanding properties of the compound of the invention as an apparent $M_1$-type agonist. Although experiments were not performed in all the tests in the same species (mice or rats) and under the same experimental conditions, a striking parallelism in the relative activity profiles does appear between pirenzepine ($M_1$-antagonist) and AF102B ($M_1$-agonist). For both compounds, memory impairments (induced by pirenzepine) and reversal of AF64A-induced memory impairments (caused by AF102B) occur at much lower doses than needed to antagonize central effects induced by oxotremorine (in the case of pirenzepine) or to induce the same kind of central side effects (in the case of AF102B).

Thus, cognitive functions mediated by an $M_1$-antagonist (pirenzepine) or an $M_1$-agonist (AF102B) are more sensitive to such cholinergic interventions than other central effects such as tremors or antinociception. This finding is extremely important since it can be used to explain why AF102B has such a remarkable selectivity and why it can be considered as an excellent candidate for a drug in SDAT.

| oxotremorine in various in vivo and in vitro tests. | | |
|---|---|---|
| Test | Pirenzepine (PNZ) ($M_1$-antagonist) ug/mouse, icv | AF102B ($M_1$-agonist) mg./kg., rats* |
| passive avoidance | 0.1(a) | 0.1–1 ip(b) |
| | | 1 po(b) |
| tremor | 5.8(c) | >60–80 ip**(d) |
| | | >78 ip(d) |
| | | >100 po(d) |
| antinociception | 4.6(c) | 60 po**(d) |
| | | 20 ip**(d) |
| | Oxotremorine | AF102B |
| $EC_{50}$, M | | |
| [$^3$H]—PNZ-binding | $8 \times 10^{-7}$ | $4 \times 10^{-7}$ |
| [$^3$H]—QNB-binding | $3 \times 10^{-6}$ | $10^{-5}$ | notes:
*unless otherwise indicated
**mice
(a) minimum effective dose of PNZ producing impaired passive avoidance learning.
(b) effective dose of AF102B producing reversal of AF64A (3 nmol/side, icv)-induced impaired passive avoidance learning (the minimum effective dose can be lower for the po route of administration).
(c) dose of PNZ required to reduce the effect of oxotremorine (0.5 mg./kg., ip) by 50% [Caulfield et al, J. Pharm. Pharmacol. 35: 131-2 (1983)].
(d) tremors and antinociception (analgesia) induced by AF102B in mice and rats; these effects are observed around the toxic doses of the compound (antinociception is performed by the tail-flick test in mice).

While the invention has been particularly described with respect to certain presently preferred embodiments, it will be appreciated by those skilled in the art that many modifications and variations can be made. Accordingly, the invention is not to be construed as limited by these embodiments, rather it is to be defined only by the claims which follow.

We claim:

1. A compound of the formula (I)

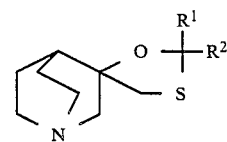

and geometrical isomers, enantiomers, diastereoisomers, racemates and/or acid addition salts thereof, wherein $R^1$ is selected from the group consisting of hydrogen, lower alkyl, cyclopentyl, cyclohexyl, phenyl, diphenylmethylol and lower alkyl which is substituted by one or two phenyl groups and R is selected from the group consisting of lower alkyl, cyclopentyl, cyclohexyl, phenyl, diphenylmethylol and lower alkyl which is substituted by one or two phenyl groups.

2. A compound according to claim 1, wherein $R^1$ is hydrogen, and $R^2$ is selected from the group consisting of lower alkyl, cyclopentyl, cyclohexyl, phenyl, diphenylmethylol and lower alkyl which is substituted by one or two phenyl groups.

3. A compound according to claim 1, wherein $R^1$ is selected from the group consisting of lower alkyl, cyclopentyl and cyclohexyl, and $R^2$ is selected from the group consisting of lower alkyl, cyclopentyl, cyclohexyl, phenyl, diphenylmethylol and lower alkyl which is substituted by one or two phenyl groups.

4. A compound according to claim 1, wherein $R^1$ is phenyl, and $R^2$ is selected from the group consisting of phenyl, diphenylmethylol and lower alkyl which is substituted by one or two phenyl groups.

5. A compound according to claim 2, wherein $R^1$ is hydrogen and $R^2$ is methyl.

6. A compound according to claim 2, wherein $R^1$ is hydrogen and $R^2$ is phenyl.

7. A compound according to claim 2, wherein $R^1$ is hydrogen and $R^2$ is diphenylmethyl.

8. A compound according to claim 2, wherein $R^1$ is hydrogen and $R^2$ is selected from the group consisting of ethyl, propyl and diphenylmethylol.

9. A compound according to claim 3, wherein $R^1$ is methyl and $R^2$ is phenyl.

10. A compound according to claim 3, wherein $R^2$ is phenyl and $R^1$ is selected from the group consisting of ethyl and cyclohexyl.

11. A compound according to claim 4, wherein $R^1$ and $R^2$ are each phenyl.

12. The geometrical isomer of the compound according to claim 5, the hydrochloric acid salt of which has the relatively lower melting-point (the cis-isomer).

13. The geometrical isomer of the compound according to claim 5, the hydrochloric acid salt of which has the relatively higher melting-point (the trans-isomer).

14. The hydrochloric acid salt of the compound according to claim 5.

15. The relatively lower melting-point geometrical isomer (the cis-isomer) of the compound according to claim 14.

16. The relatively higher melting-point geometrical isomer (the trans-isomer) of the compound according to claim 14.

17. A pharmaceutical composition comprising a compound of formula (I) according to claim 1, or a pharmaceutically compatible acid addition salt thereof, together with an inert carrier or diluent.

18. A pharmaceutical composition according to claim 17, which is in a form suitable for oral, rectal or parenteral administration, or for administration by insufflation.

19. A pharmaceutical composition according to claim 17, which is in a form suitable for transdermal administration.

20. A pharmaceutical composition according to claim 17, which is in unit dosage form.

21. A pharmaceutical composition for transdermal administration, comprising a compound of formula (I) according to claim 1, or a pharmaceutically compatible acid addition salt thereof, and a low molecular weight fatty acid.

22. A pharmaceutical composition according to claim 17, wherein the compound of formula (I) is that in which $R^1$ is phenyl, and $R^2$ is selected from the group consisting of ethyl, cyclohexyl and phenyl.

23. A pharmaceutical composition according to claim 17, wherein the compound of formula (I) is that in which R is hydrogen, and $R^2$ is selected from the group consisting of methyl and ethyl.

24. A pharmaceutical composition according to claim 17, wherein the compound of formula (I) is that defined in claim 12.

25. A pharmaceutical composition according to claim 24, further comprising one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

26. A pharmaceutical composition according to claim 17, wherein the compound of formula (I) is that in which $R^2$ is selected from the group consisting of lower alkyl containing at least three carbon atoms, cyclopentyl, cyclohexyl, phenyl, diphenylmethylol and lower alkyl substituted by one or two phenyl groups, and $R^1$ is selected from the group consisting of hydrogen, lower alkyl, cyclopentyl, cyclohexyl, phenyl, diphenylmethylol and lower alkyl substituted by one or two phenyl groups.

27. A pharmaceutical composition according to claim 26, wherein the compound formula (I) is that in which $R^1$ is ethyl and $R^2$ is phenyl.

28. A pharmaceutical composition according to claim 26, wherein the compound of formula (I) is that in which $R^1$ is hydrogen and $R^2$ is diphenylmethyl.

29. A pharmaceutical composition according to claim 26, wherein the compound of formula (I) is that in which $R^1$ is hydrogen, and $R^2$ is selected from the group consisting of propyl, phenyl, and diphenylmethylol.

30. A method for treating diseases of the central nervous system in mammals, comprising administering to the mammal a compound of formula (I) according to claim 1 or a pharmaceutically compatible acid addition salt thereof.

31. A method for treating diseases of the central nervous system in mammals, comprising administering to the mammal a pharmaceutical composition according to in claim 17.

32. A method for treating diseases of the central nervous system is mammals, comprising transdermal administration to the mammal of a compound of formula (I) according to claim 1 or a pharmaceutically compatible acid addition salt thereof.

33. A method for treating diseases due to a deficiency in the central cholinergic system in mammals, comprising administering to the mammal a compound according to claim 2, wherein $R^1$ is hydrogen and $R^2$ is methyl, or geometrical isomers, enantiomers, racemates or acid addition salts thereof.

34. A method for treating diseases due to a deficiency in the central cholinergic system in mammals, comprising administering to the mammal a pharmaceutical composition containing a compound according to claim 2, wherein $R^1$ is hydrogen and $R^2$ is methyl, or geometrical isomers, enantiomers, racemates or acid addition salts thereof, together with an inert carrier or diluent.

35. A method for treating diseases due to a deficiency in the central cholinergic system in mammals, comprising transdermal administration to the mammal of a compound according to claim 2, wherein $R^1$ is hydrogen and $R^2$ is methyl, or geometrical isomers, enantiomers, racemates or acid addition salts thereof.

36. A method for treating diseases due to cholinergic hyperfunction in mammals, comprising administering to the mammal a compound of formula (I) according to claim 1 or a pharmaceutically compatible acid addition salt thereof, wherein $R^2$ is selected from the group consisting of lower alkyl containing at least three carbon atoms, cyclopentyl, cyclohexyl, phenyl, diphenylmethylol and lower alkyl substituted by one or two phenyl groups, and $R^1$ is selected from the group consisting of hydrogen, lower alkyl, cyclopentyl, cyclohexyl, phenyl, diphenylmethylol and alkyl substituted by one or two phenyl groups.

37. A method for treating diseases due to cholinergic hyperfunction in mammals, comprising administering to the mammal a pharmaceutical composition containing a compound of formula (I) according to claim 1 or a pharmaceutically compatible acid addition salt thereof, wherein $R^2$ is selected from the group consisting of lower alkyl containing at least three carbon atoms, cyclopentyl, cyclohexyl, phenyl, diphenylmethylol and lower alkyl substituted by one or two phenyl groups, and $R^1$ is selected from the group consisting of hydrogen, lower alkyl, cyclopentyl, cyclohexyl, phenyl, diphenylmethylol and alkyl substituted by one or two phenyl groups, together with an inert carrier or diluent.

38. A method for treating diseases due to cholinergic hyperfunction in mammals, comprising transdermal administration to the mammal of a compound of formula (I) or a pharmaceutically compatible acid addition salt thereof, wherein $R^2$ is selected from the group consisting of lower alkyl containing at least three carbon atoms, cyclopentyl, cyclohexyl, phenyl, diphenylmethylol and lower alkyl substituted by one or two phenyl groups, and $R^1$ is selected from the group consisting of hydrogen, lower alkyl, cyclopentyl, cyclohexyl, phenyl, diphenylmethylol and lower alkyl substituted by one or two phenyl groups.

39. A method of treating diseases due to cholinergic hyperfunction in mammals, comprising administering to the mammal a compound according to claim 7, or a pharmaceutically compatible acid addition salt thereof.

40. A method for treating diseases due to cholinergic hyperfunction in mammals, comprising administering to the mammal a pharmaceutical composition containing a compound according to claim 7, or a pharmaceutically compatible acid addition salt thereof, together with an inert carrier or diluent.

41. A method for treating diseases due to a deficiency in the central cholinergic system in mammals, comprising transdermal administration to the mammal of a compound according to claim 7, or a pharmaceutically compatible acid addition salt thereof.

42. A method for treating diseases due to cholinergic hyperfunction in mammals, comprising administering to the mammal a compound according to claim 9, or a pharmaceutically compatible acid addition salt thereof.

43. A method for treating diseases due to cholinergic hyperfunction in mammals, comprising administering to the mammal a pharmaceutical composition containing a compound according to claim 9, or a pharmaceutically compatible acid addition salt thereof, together with an inert carrier or diluent.

44. A method for treating diseases due to cholinergic hyperfunction in mammals, comprising transdermal administration to the mammal of a compound according to claim 9, or a pharmaceutically compatible acid addition salt thereof.

45. A method for treating senile dementia of Alzheimer's type, comprising administering to a patient a compound according to claim 13, or pharmaceutically compatible acid addition salt thereof.

46. A method for treating senile dementia of Alzheimer's type, comprising administering to a patient a pharmaceutical composition containing a compound according to claim 12, or a pharmaceutically compatible acid addition salt thereof, together with an inert carrier or diluent.

47. A method for treating senile dementia of Alzheimer's type, comprising transdermal administration to a patient of a compound according to claim 12, or a pharmaceutically compatible acid addition salt thereof.

48. A method according to claim 45 wherein there is coadministered with said compound, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

49. A method according to claim 46 wherein there is coadministered with said compound, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

50. A method according to claim 47 wherein there is coadministered with said compound, one or more compounds selected from the group consisting of physostigmine, tetrahydroaminoacridine, 4-aminopyridine and 3,4-diaminopyridine.

51. A pharmaceutical composition in unit dosage form comprising a compound of formula (I) according to claim 1, or a pharmaceutically compatible acid addition salt thereof, in an amount ranging from about 0.5 to about 500 mg., together with an inert carrier or diluent.

52. A pharmaceutical composition according to claim 51 comprising the said compound, or a pharmaceutically compatible acid addition salt thereof, in an amount in the range of about 5 to about 100 mg.

53. A pharmaceutical composition according to claim 52 comprising the said compound, or a pharmaceutically compatible acid addition salt thereof, in an amount in the range of about 10 to about 50 mg.

54. A pharmaceutical composition according to claim 51, further comprising one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

55. A pharmaceutical composition according to claim 51, wherein the composition is adapted for oral administration.

56. A pharmaceutical composition according to claim 51, wherein the composition is adapted for parenteral administration.

57. A method for treating senile dementia of Alzheimer's type, comprising orally administering to a patient a compound according to claim 12, or a pharmaceutically compatible acid addition salt thereof, in an amount ranging from about 0.1 to about 60 mg./kg. body weight.

58. A method according to claim 57 wherein said amount ranges from about 0.5 to about 10 mg./kg. body weight.

59. A method according to claim 58 wherein said amount ranges from about 1 to about 5 mg./kg. body weight.

60. A method according to claim 57, wherein there is coadministered with the said compound, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

61. A method according to claim 59, wherein administration is by means of a pharmaceutical composition in unit dosage form comprising the said compound in an amount about 0.5 to about 500 mg., together with an inert carrier or diluent.

62. A method for treating senile dementia of Alzheimer's type, comprising parenterally administering to a patient a compound according to claim 12, or a pharmaceutically compatible acid addition salt thereof, in an amount ranging from about 0.01 to about 40 mg./kg. body weight.

63. A method according to claim 62 wherein said amount ranges from about 0.05 to about 5 mg./kg. body weight.

64. A method according to claim 63 wherein said amount ranges from about 0.1 to about 2 mg./kg. body weight.

65. A method according to claim 62, wherein there is coadministered with the said compound, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine and somatostatin.

66. A method according to claim 62, wherein administration is by means of a pharmaceutical composition in unit dosage form comprising the said compound in an amount ranging from about 0.5 to about 500 mg., together with an inert carrier or diluent.

67. The compound 3-hydroxy-3-mercaptomethyl quinuclidine.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 4,855,290 |
| (45) | ISSUED | : | August 8, 1989 |
| (75) | INVENTOR | : | Abraham Fisher, et al. |
| (73) | PATENT OWNER | : | STATE OF ISRAEL, REPRESENTED BY PRIME MINISTER'S OFFICE, ISRAEL INSTITUTE FOR BIOLOGICAL RESEARCH |
| (95) | PRODUCT | : | EVOXAC® (Cevimeline HCl) |

This is to certify that an application under 35 U.S.C. § 156 has been filed in the United States Patent and Trademark Office, requesting extension of the term of U.S. Patent No. 4,855,290 based upon the regulatory review of the product EVOXAC® (Cevimeline HCl) by the Food and Drug Administration. Since it appears that the requirements of the law have been met, this certificate extends the term of the patent for the period of

(94)                        1,118 days from August 8, 2006, the original expiration date of the patent, subject to the payment of maintenance fees as provided by law, with all rights pertaining thereto as provided by 35 U.S.C. § 156(b).

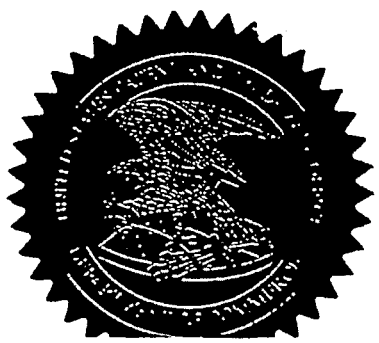

I have caused the seal of the United States Patent and Trademark Office to be affixed this 30th day of November 2005.

Jon W. Dudas
Under Secretary of Commerce for Intellectual Property and Director of the United States Patent and Trademark Office

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 4,855,290 |
| (45) | ISSUED | : | August 8, 1989 |
| (75) | INVENTOR | : | Abraham Fisher, et al. |
| (73) | PATENT OWNER | : | STATE OF ISRAEL, REPRESENTED BY PRIME MINISTER'S OFFICE, ISRAEL INSTITUTE FOR BIOLOGICAL RESEARCH |
| (95) | PRODUCT | : | EVOXAC® (Cevimeline HCl) |

This is to certify that an application under 35 U.S.C. § 156 has been filed in the United States Patent and Trademark Office, requesting extension of the term of U.S. Patent No. 4,855,290 based upon the regulatory review of the product EVOXAC® (Cevimeline HCl) by the Food and Drug Administration. Since it appears that the requirements of the law have been met, this certificate extends the term of the patent for the period of

(94)                   1,118 days from August 8, 2006, the original expiration date of the patent, subject to the payment of maintenance fees as provided by law, with all rights pertaining thereto as provided by 35 U.S.C. § 156(b).

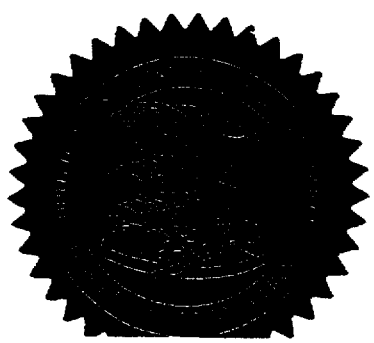

I have caused the seal of the United States Patent and Trademark Office to be affixed this 30th day of November 2005.

Jon W. Dudas
Under Secretary of Commerce for Intellectual Property and Director of the United States Patent and Trademark Office